United States Patent [19]
Bergersen

[11] Patent Number: 5,882,192
[45] Date of Patent: Mar. 16, 1999

[54] COMPUTERIZED ORTHODONTIC DIAGNOSIS AND APPLIANCE DISPENSER

[75] Inventor: Earl O Bergersen, Winnetka, Ill.

[73] Assignee: Ortho-Tain, Inc., Bayamon, Puerto Rico

[21] Appl. No.: 961,092

[22] Filed: Oct. 30, 1997

[51] Int. Cl.[6] .................................................. A61C 3/00
[52] U.S. Cl. ................................. 433/2; 433/6; 433/214
[58] Field of Search ................................ 433/2, 6, 3, 24, 433/68, 214, 223

[56] References Cited

U.S. PATENT DOCUMENTS

| | | |
|---|---|---|
| 3,898,736 | 8/1975 | Bergersen . |
| 3,939,598 | 2/1976 | Bergersen . |
| 4,073,061 | 2/1978 | Bergersen . |
| 4,182,036 | 1/1980 | Tada et al. .................................... 433/2 |
| 4,663,720 | 5/1987 | Duret et al. .............................. 433/214 |
| 4,742,464 | 5/1988 | Duret et al. .............................. 433/214 |
| 4,837,732 | 6/1989 | Brandestini et al. .................... 433/223 |
| 4,935,635 | 6/1990 | O'Harra .................................... 433/214 |
| 5,037,295 | 8/1991 | Bergersen . |
| 5,278,756 | 1/1994 | Lemchen et al. ......................... 433/68 |
| 5,320,462 | 6/1994 | Johansson et al. ...................... 433/223 |
| 5,683,243 | 11/1997 | Andreiko et al. ........................... 433/3 |

Primary Examiner—Ralph A. Lewis
Attorney, Agent, or Firm—Hill & Simpson

[57] ABSTRACT

A method and apparatus for diagnosing orthodontic conditions of an individual. The apparatus includes an outer case and a user interface disposed on the outer case for communicating with the individual. The apparatus further has diagnostic hardware including at least one digital camera carried within the case adapted to take a plurality of video images of the teeth and mouth of the individual. The apparatus further has electronic circuitry which is preprogrammed with statistical data for comparison to actual data collected by the diagnostic hardware and transmitted to the electronic circuitry. The circuitry is further adapted to diagnose whether the individual has correctable orthodontic conditions. The apparatus is further adapted to dispense instructions to the individual for receiving proper corrective orthodontic care. The method of the invention includes providing an apparatus adapted to take various digital images of the individual's teeth and mouth. The digital images are analyzed by the electronic circuitry and compared to the statistical data preprogrammed within the apparatus for diagnosing whether the individual has correctable orthodontic conditions. The method further includes the steps of informing the individual as to whether their orthodontic conditions are correctable and instructing the individual on how to correct the orthodontic conditions diagnosed and dispensing an appropriate appliance.

27 Claims, 20 Drawing Sheets

COMPUTERIZED ORTHODONTIC DIAGNOSIS AND APPLIANCE DISPENSER

FIELD OF THE INVENTION

The present invention relates to orthodontic devices, and in particular to an apparatus for diagnosing orthodontic requirements and dispensing an orthodontic appliance to suit the diagnosed requirements.

BACKGROUND OF THE INVENTION

Diagnosis and treatment of tooth misalignment is either unavailable, or if available is too costly for inhabitants in many parts of the world. In some regions, there are a limited number of medical facilities and an even fewer number of dental facilities and practitioners available for treating orthodontic conditions. Because of this deficiency there are innumerable cases of misaligned teeth which but for this fact would be easily treatable.

Prefabricated tooth positioning retainers invented by the inventor of the instant application are available in various standard sizes and are utilized to properly position and straighten teeth if properly worn. These devices have been proved effective in correcting many types of tooth misalignment conditions especially in children and adults. These devices have also significantly reduced the cost of providing orthodontic care which traditionally requires many visits to an orthodontist and complicated hardware installed in the mouth of a patient.

One problem is that though these appliances are available and effective they require a thorough diagnosis for selecting the proper sized appliance for a particular patient. There are a limited number of medical facilities, dental facilities and especially individuals trained in orthodontic care in many parts of the world, therefore no such diagnosis may be readily available or even possible for the patient. What is desirable is to provide a method and apparatus for individuals in need of orthodontic care to obtain the proper diagnosis and treatment while requiring either no or only minimal visits to an orthodontic specialist. Another problem is that in remote parts of the world, billing procedures and obtaining payment for diagnosis and treatment may be difficult at best. What is also desirable is to provide a method and an apparatus for providing such proper diagnosis and treatment which further provides a simple and efficient way for a patient to pay for the services and for the provider of the service to be compensated.

SUMMARY OF THE INVENTION

The present invention is for a method and apparatus of diagnosing and dispensing standardized orthodontic appliances.

The apparatus of the invention includes an outer protective housing having a user interface thereon for receiving information from a user of the apparatus and for communicating information to the user. The apparatus also includes diagnosis hardware for measuring the teeth and determining the orthodontic conditions of the user, converting the information into useful data, and transmitting the data to the apparatus. The apparatus further houses pre-programmed circuitry and electronics for receiving the data, performing a particular diagnosis, and determining the proper appliance size for the particular user. Within the outer housing of the apparatus is a storage chamber for holding a predetermined quantity of each standard size of the orthodontic appliances. The apparatus also has a dispensing mechanism communicating with the preprogrammed electronics for selecting the proper orthodontic appliance and for dispensing the selected appliance to the user. The apparatus further includes a means for instructing the patient on how to properly use the appliance and other necessary instructions. The apparatus also includes a means by which the patient can submit payment directly to the machine for the diagnosis and for any appliance dispensed.

In one embodiment the diagnosis, hardware of the apparatus includes one or more digital image cameras for photographing the mouth area and teeth of the patient. In another embodiment the apparatus includes several small cameras which move according to preprogrammed coordinates in order to take video images from all necessary angles and views for diagnosing the patient. In an alternative embodiment the apparatus includes one or more stationary video cameras which photograph the patient's mouth and teeth areas as the patient moves according to instructions provided by the apparatus.

In one embodiment the apparatus includes a touch screen for providing visual instructions to the patient during the use of the apparatus and for receiving information provided by the patient and transmitting the information to the circuitry and electronics of the apparatus for performing the particular diagnosis. In another embodiment the user interface of the apparatus includes a keyboard provided in the particular language of the patient for receiving information input by the patient and for transmitting the information to the circuitry and electronics. In a further embodiment the apparatus of the invention includes a means for dispensing written instructions and information to the patient on a tangible product such as paper.

In one embodiment the apparatus includes means for receiving a credit card and for deducting the proper amount of payment from the card and for transmitting the appropriate payment information to the card holder through the circuitry and electronics. In an alternative embodiment, the circuitry and electronics stores payment information from a patient's credit card for later download. In another embodiment the apparatus includes means for receiving payment via prepaid debit card which may be provided to the patient prior to seeking the diagnosis and treatment via the apparatus of the invention.

The method of the invention comprises the various steps of diagnosing the particular orthodontic requirements of a patient, selecting the correct orthodontic appliance from a series of standard appliances stored within the machine, dispensing the selected appliance to the patient, and dispensing along with the necessary instructions for proper use of the appliance. In one embodiment the method comprises obtaining necessary information from the patient prior to beginning the diagnosis such as age, height, sex and pertinent family characteristics. In this embodiment the patient will be asked the pertinent questions via a user interface of the machine. In another embodiment of the invention the diagnosis of the patient includes the step of photographing the patient's mouth and teeth from several different angles and views. In one embodiment the views are taken as still photographs in digital format by one or more fixed cameras which transmit the digital image information to the apparatus.

In another embodiment the diagnosis steps of the invention are preformed by several movable cameras within the apparatus which take the various necessary views of the patients mouth and teeth while the patient remains relatively stationary. In a further embodiment the cameras of the apparatus perform the diagnosis steps by taking moving digital images which are interpreted by the apparatus.

In one embodiment of the invention the apparatus is preprogrammed to proceed through the many steps of a diagnosis program to determine the particular orthodontic needs of the patient. In one embodiment the programming of the apparatus compares the digital image data of the patient to digitally stored images of many normal and extreme cases of orthodontic conditions for various ages and sexes and the like. In another embodiment the program of the apparatus compares the digital image data of the patient to preprogrammed limits for various orthodontic conditions. The program will then determine from the data comparisons the particular orthodontic needs of the patient.

DETAILED DESCRIPTION OF THE PRESENTLY PREFERRED EMBODIMENTS

Figure 1:
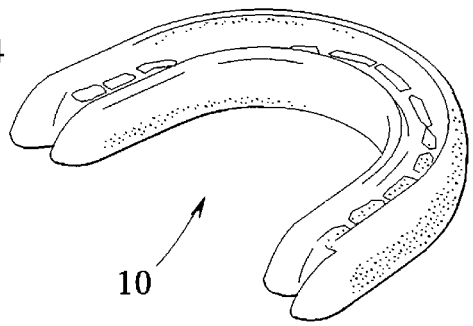
FIG. 1 is a perspective view of an orthodontic appliance which is utilized by the method and apparatus of the present invention.

FIG. 1 illustrates an orthodontic appliance 10 the details of which are disclosed in many of my prior patents including exemplary U.S. Pat. Nos. 3,898,736; 3,939,598; 4,073,061; and 5,037,295. Such appliances are produced in various standardized sizes depending upon a particular individual's tooth size, tooth spacing, and tooth alignment conditions. The present invention is directed to a method and apparatus for diagnosing a particular patient's orthodontic requirements, selecting the proper appliance for correcting the orthodontic conditions, and dispensing the selected appliance.

Figure 2:
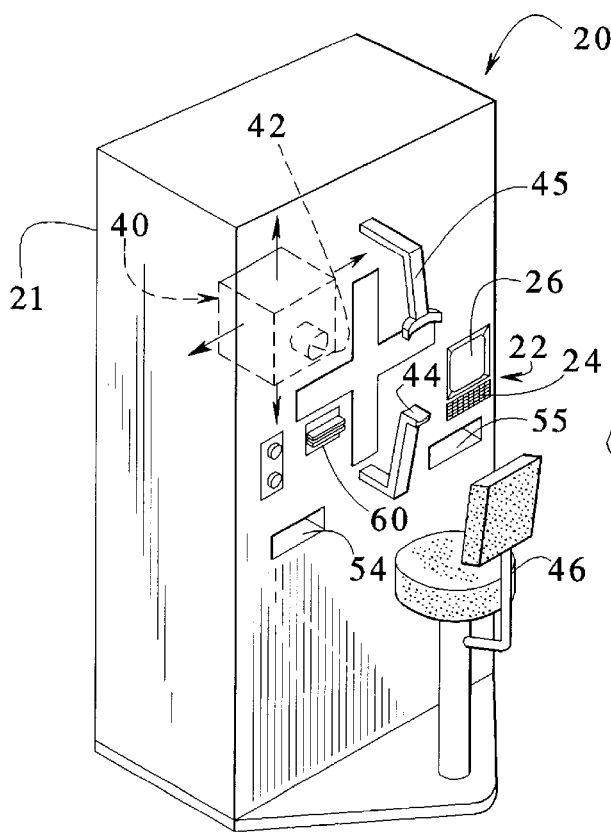
FIG. 2 is a perspective view of an orthodontic diagnosis and appliance dispenser constructed in accordance with the present invention.

FIG. 2 illustrates a generic view of an apparatus 20 constructed in accordance with one embodiment of the present invention. The apparatus includes an outer protective housing 21 which may take on any number of configurations and constructions but is preferably of a relatively sturdy and secure construction to prevent theft from or tampering with the apparatus. For example, housing 21 may be of a steel construction welded or bolted together to enclose the remaining components of the apparatus within the housing.

A user interface 22 is located on one exterior surface of housing 21 for manipulation by a user of apparatus 20. User interface 22 includes a data entry surface 24 through which a user may input information necessary for properly operating the apparatus. User interface 22 may also include a display 26 such as an LED or an LCD display for relaying information from the apparatus to the user. Data entry surface 24 may include a plurality of lettered and numbered input keys for manual data entry as will be described below, or may be a touch screen or other suitable construction.

Apparatus 20 also includes diagnosis hardware 40 disposed within housing 21. Hardware 40 is adapted to collect data from the user's mouth and transmit the data to the internal electronics of apparatus 20 as will also be described below. In one embodiment, diagnosis hardware 40 includes a video camera 42 mounted to housing 21 for taking a series of video images or photographs of the user's mouth and teeth. Camera 42 is preferably hard wired to the internal electronics of apparatus 20 for transmitting the video image information thereto for diagnosing the particular users orthodontic needs.

Although the present invention is not intended to be limited to the type of video camera and electronic signals utilized, it is preferred that the video camera 42 produces a digital image of the various views of the user's mouth. Such cameras are generally very small, durable and light weight and are available from a number of sources. An example of such a camera is a charge coupled device or CCD camera. Another suitable camera would be an ultra-high resolution type digital camera which is also available from several sources. Both types of cameras produce digital images which are readily suitable for the present invention. CCD type cameras are available from Panasonic Industries Camera Division, Chori America, Inc., Data Cell Image Manufacturing Company, JVC, Sony Electronics, and Eastman Kodak Company to name a few. Similarly, ultra-high resolution video equipment is available from Eastman Kodak, Data Cell, Toshiba America, and Carl Zeiss as well as a number of other sources.

A chin support member 44 and forehead rest 45 is positioned adjacent camera 42 on housing 21 for properly positioning and holding stationary the user's head during use of apparatus 20 for obtaining an accurate diagnosis. Housing 21 may also include a seat 46 on which a user may comfortably rest while undergoing the diagnosis.

In one embodiment, camera 42 is stationary relative to apparatus 20. With such a construction the user is instructed by the apparatus via user interface 22 to move their head and jaw appropriately to allow camera 42 to acquire all of the necessary images. In another embodiment, the users head is held stationary on chin support member 44 while one or more cameras 42 move relative to apparatus 20 according to preprogrammed positions for acquiring the necessary images of the user's mouth. It is necessary however that camera 42 acquire various still digital photographs from several angles or various continuous video digital images of the individual's face and teeth. The images must include occlusal views as well as labial and buccal surface views of the teeth. It is preferred that the video images taken also enable the apparatus to determine facial symmetry, facial length, profile and lip contour, chin and nose contour and potentially other necessary aspects of the individuals face for providing a proper and complete diagnosis.

From the various video images, apparatus 20 generates a diagnosis and analysis of the individuals occlusal conditions, existence of particular teeth, size and spacing of teeth, and other important data as will be described below. In one embodiment, apparatus 20 may provide, or a supply may be placed nearby, a special paper which the user moistens and then places on their teeth as instructed. The paper may be marked or otherwise provide reference points for the electronics of the apparatus to perform the diagnosis.

Apparatus 20 further includes various internal circuitry and electronics 51 pre-programmed to collect, analyze and evaluate data received through user interface 22 and diagnostic hardware 40. The operation of internal preprogrammed electronics 51 is described in greater detail below, but upon analyzing and evaluating the data the apparatus will select the appropriate prefabricated orthodontic appliance and dispense the appliance to the individual.

Apparatus 20 also includes a storage chamber (not shown) within housing 21 for holding an adequate supply of prefabricated appliances 10 in the various standard sizes (or a single one size fits all type of appliance). Apparatus 20 may further include a dispensing mechanism (not shown) and a dispensing slot 54 in housing 21 for delivering the appropriate appliance to the user.

In another embodiment, apparatus 20 of the invention may merely be used for diagnosing the orthodontic needs and requirements of individuals and therefore will not include a storage chamber filled with appliances 10 nor a dispensing mechanism or a slot 54. Such an apparatus would be useful in assisting orthodontic practitioners worldwide by permitting them to easily diagnose an individual's dentition conditions and to manually deliver the appropriate appliance or appliances and instructions to the individual. Having such an apparatus available to orthodontic practitioners allows them to provide treatment at a fraction of the cost of traditional wire type braces or molded retainers which are specifically designed for particular individuals.

In another embodiment, apparatus 20 also incorporates a payment device 60 accessible by the user on housing 21. Payment device 60 may take on a number of different constructions and configurations without departing from the scope of the present invention. However, preferably since the use of apparatus 20 is intended for areas which are remote and located in depressed parts of the world, payment device 60 is preferably adapted to a receive a credit or debit card having a magnetic strip as is known in the art.

Preprogrammed electronics 51 are preferably adapted to read the magnetic strip of the card and depending on the type of card either debit the account related to the card or debit the amount from the card itself. A typical debit card is known in the art and commonly used for services such as public transportation and public copy machines and the like. The card may carry a balance and when inserted into the appropriate device, a portion of the balance will be deducted in the amount of the charge for the particular service. A conventional credit card merely provides the account number and other appropriate account information so that the apparatus 20 may appropriately bill for this service.

Figure 3:
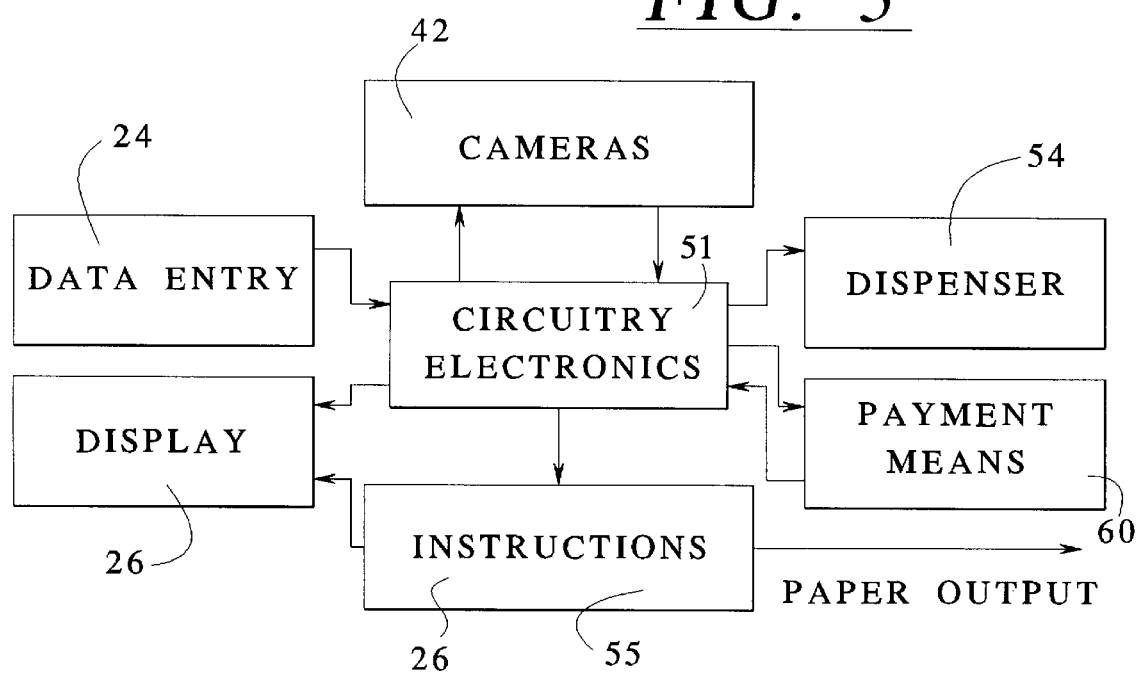
FIG. 3 is a simplified schematic diagram of the operation of the apparatus of the invention.

FIG. 3 illustrates a simplified schematic for the electronics of apparatus 20. An individual inputs information into user interface 22. The interface may include a keyboard 245 which transmits the data to the preprogrammed circuitry and electronics 51. Electronics 51 will further transmit data and instructions to display 26 of user interface 22 for communicating with the individual. Once all the necessary information has been provided by the individual, electronics 51 transmit information to cameras 42 for taking the various digital images of the individual's mouth and teeth. If necessary, the electronics may continually ask questions or instruct the individual how to move in order to acquire all of the proper video images. This may be done again through display 26 and keyboard or other data input device 24.

Cameras 42 then transmit the digital signals representing the images taken from the individual's mouth and teeth to preprogrammed electronics 51. The electronics perform the necessary calculations and diagnosis based upon the digital images, preprogrammed information, and information input by the, individual. Once the diagnosis is complete, the electronics instruct the patient whether they are a candidate for correction and treatment of their orthodontic conditions via use of one of the appliances or whether they have been rejected for treatment. These instructions may be delivered via either a hard copy such as a paper output 55 or via user display 26. The electronics also transmit a signal if necessary to the dispensing mechanism in the storage chamber for selecting an appropriate appliance and for dispensing the appliance through slot 54 of the machine.

The electronics further communicate with payment device 60 of the apparatus as well. The apparatus determines a cost or fee for the diagnosis and instructions provided to the patient as well as any additional cost for an appliance which may have been supplied through the dispenser to the patient. This cost or fee is then displayed on display 26 or may be printed out on a hard copy if the apparatus is so equipped. The user of the apparatus then inserts the appropriate credit or debit card into the machine for payment of the fee as previously described.

As will be evident to those skilled in the art, FIG. 3 is a very basic schematic of how the various components and sections of apparatus 20 are associated with one another. The particular construction and configuration of the apparatus' structure, hardware and software may vary considerably without departing from the scope of the present invention.

As illustrated in FIGS. 4–11 and 12–22, the computerized orthodontic diagnostic and appliance dispensing (CODAD) apparatus 20 may be programmed to properly diagnose an individual and also to select and dispense the proper appliance based on the diagnosis. FIGS. 4–11 illustrate a first logic flowchart or Program X for the diagnostic parameters of the CODAD apparatus for males and females from about 5 to 8 years of age with mostly deciduous anterior teeth. FIGS. 12–22 illustrate a second logic flowchart or Program Y for the diagnostic parameters for males and females from about 7 years of age and older.

Prior to embarking on the diagnostic analysis of the patient, the apparatus is preferably programmed to receive important information from the patient and to dispense information to the patient prior to diagnosis regarding the pitfalls and limitations of this form of diagnosis and treatment. The patient or an adult accompanying the patient may be asked to verify if they have read and understood the warnings and asked to indicate that the associated risks involved in this treatment technique have been understood and accepted. The apparatus may be programmed to proceed with diagnosis and dispensing of an appliance only upon acceptance by an adult.

Prior to starting the diagnostic program, the patient or the adult accompanying the patient will be asked to provide certain information to the CODAD apparatus through the data interface. This information may include the name, sex, birth date, address, and other general information for the patient. This information may further include statistical physical characteristic information such as patient's height, parent's height, whether the patient has siblings, the age, sex and height of the siblings, medical history, and other pertinent statistical information to determine by statistical comparison where the child fits in relative to the mean or median statistical information of other children programmed into the computer's electronics 51. Some of these initial questions along with information regarding the amount of upper and lower deciduous teeth in the patient, will determine at which program the computer starts, whether it be the diagnostic Program X for children in the ages of around 5 to 8 years old or diagnostic Program Y for children around 7 years old and up.

Figure 4:
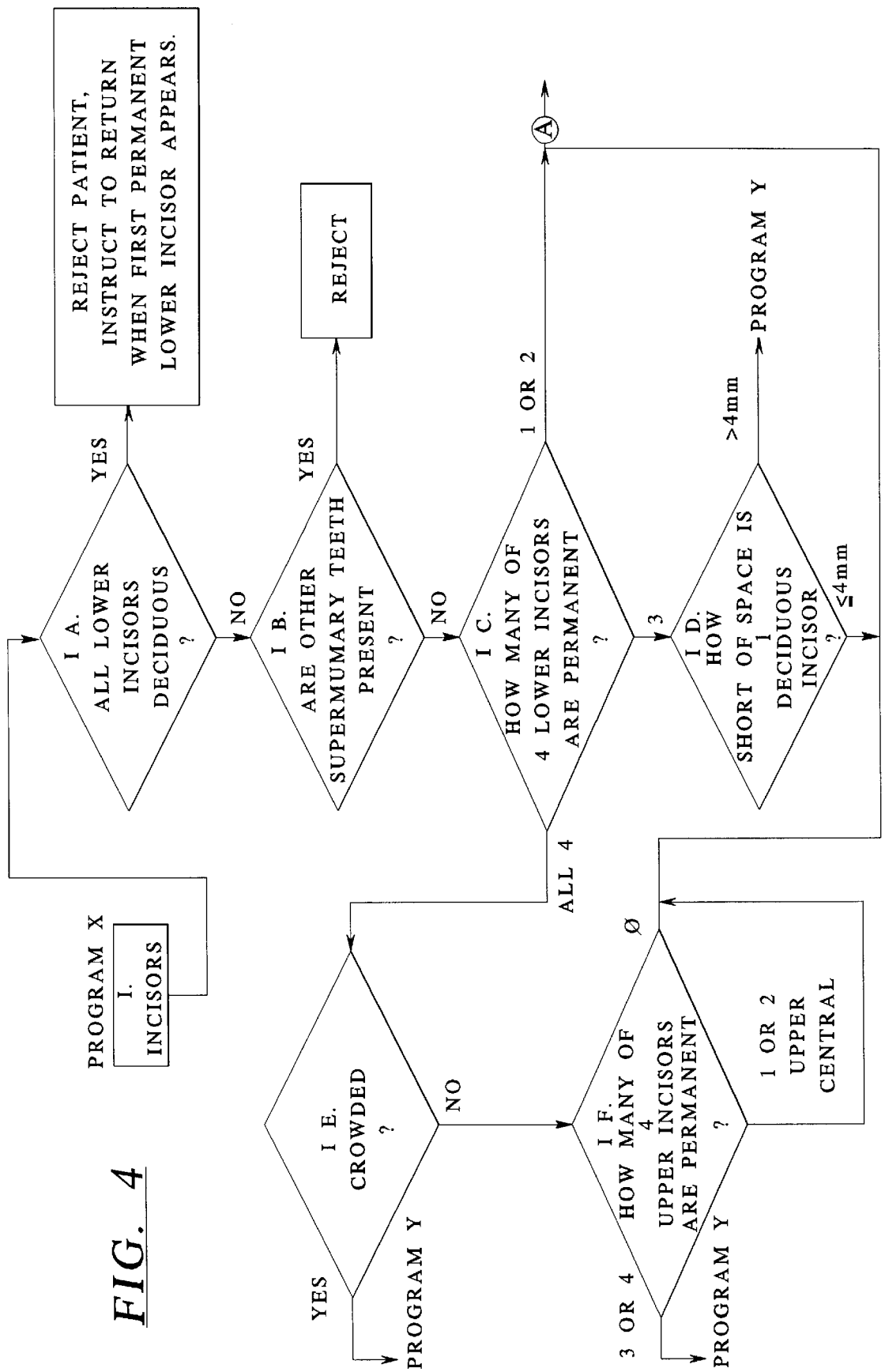
FIGS. 4–11 are a flowchart diagram of the diagnosis procedure followed by the apparatus for individuals in the age range of about 5–8 years old.
Figure 5:
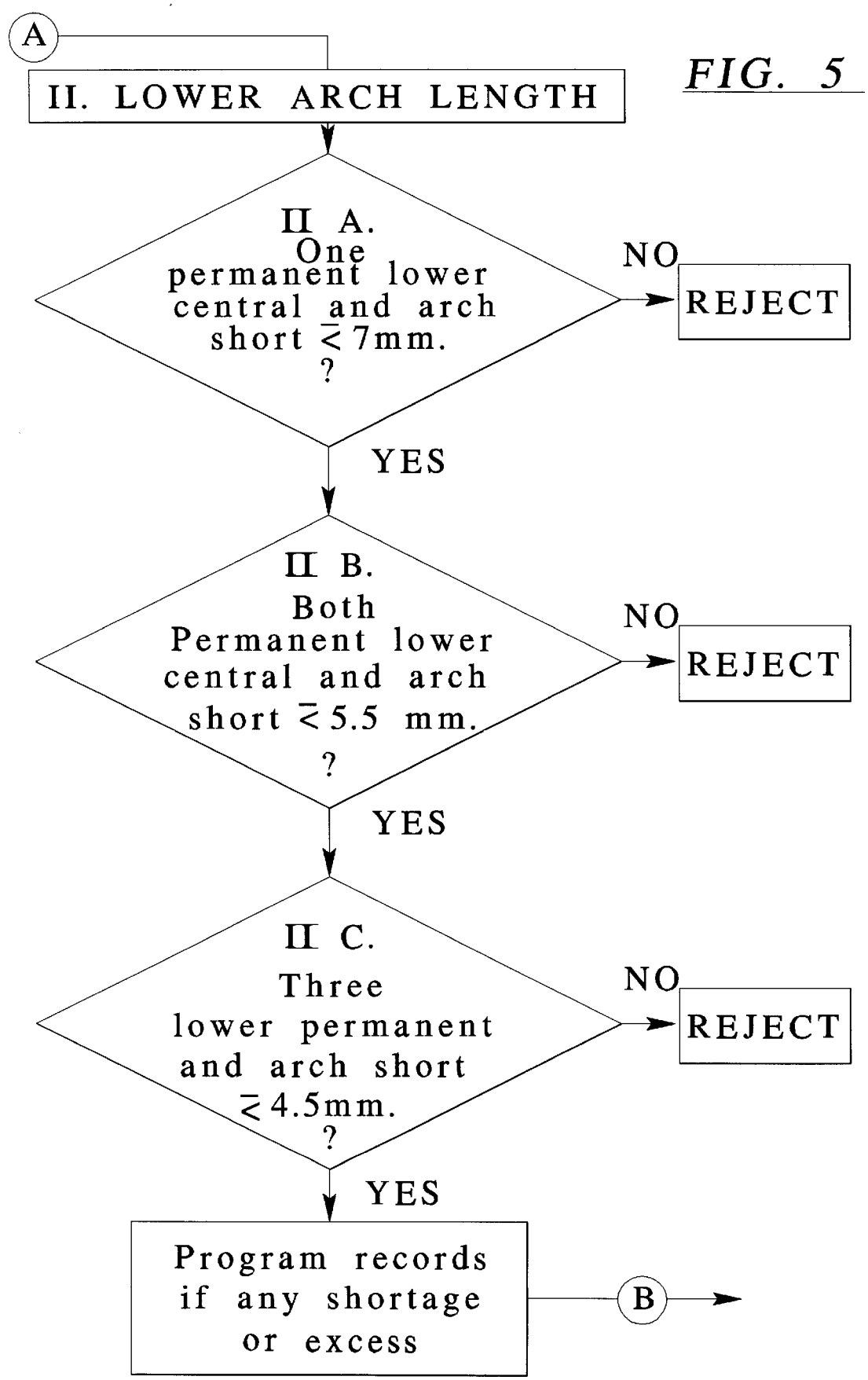
Figure 6:
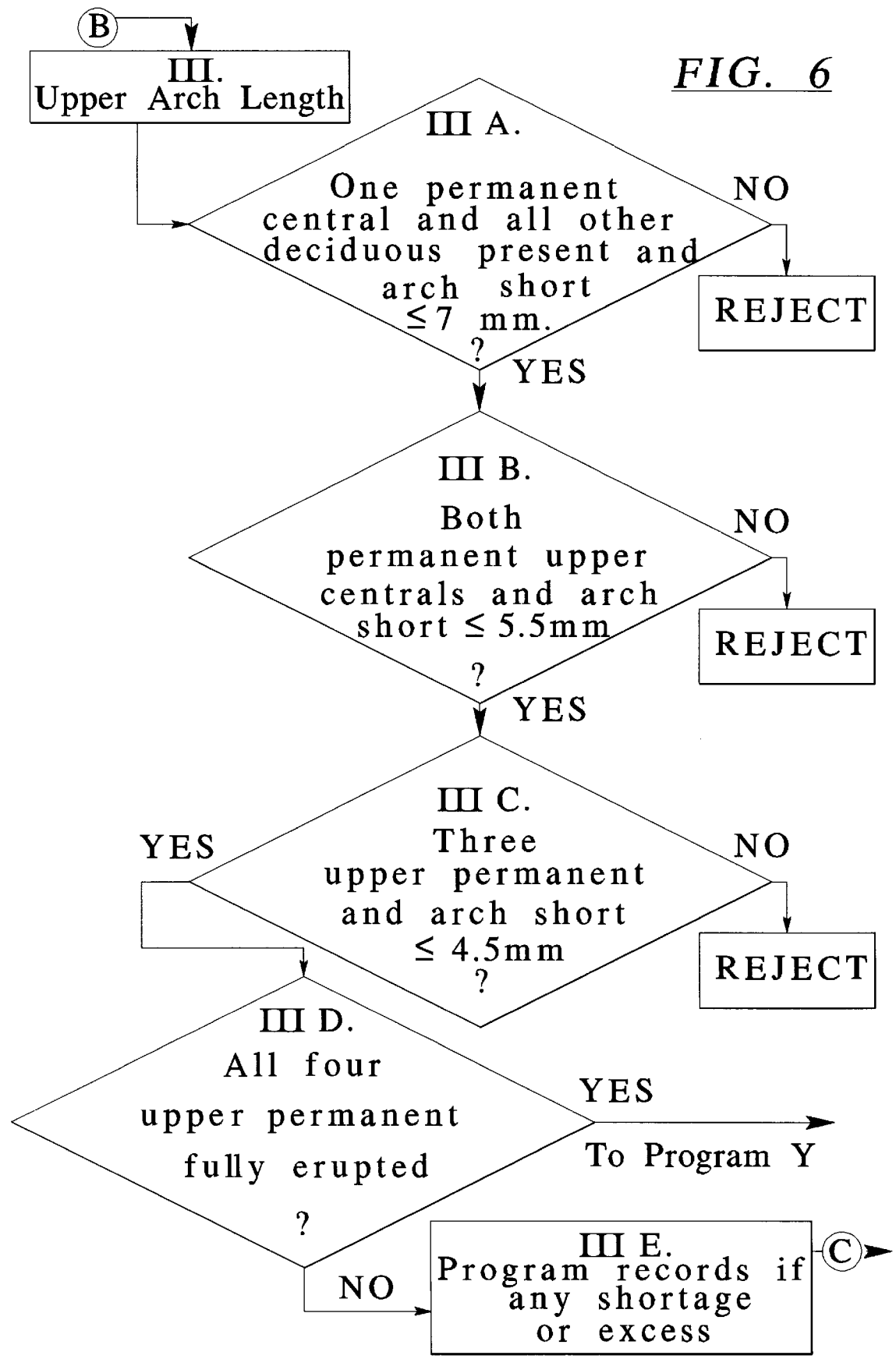
Figure 7:
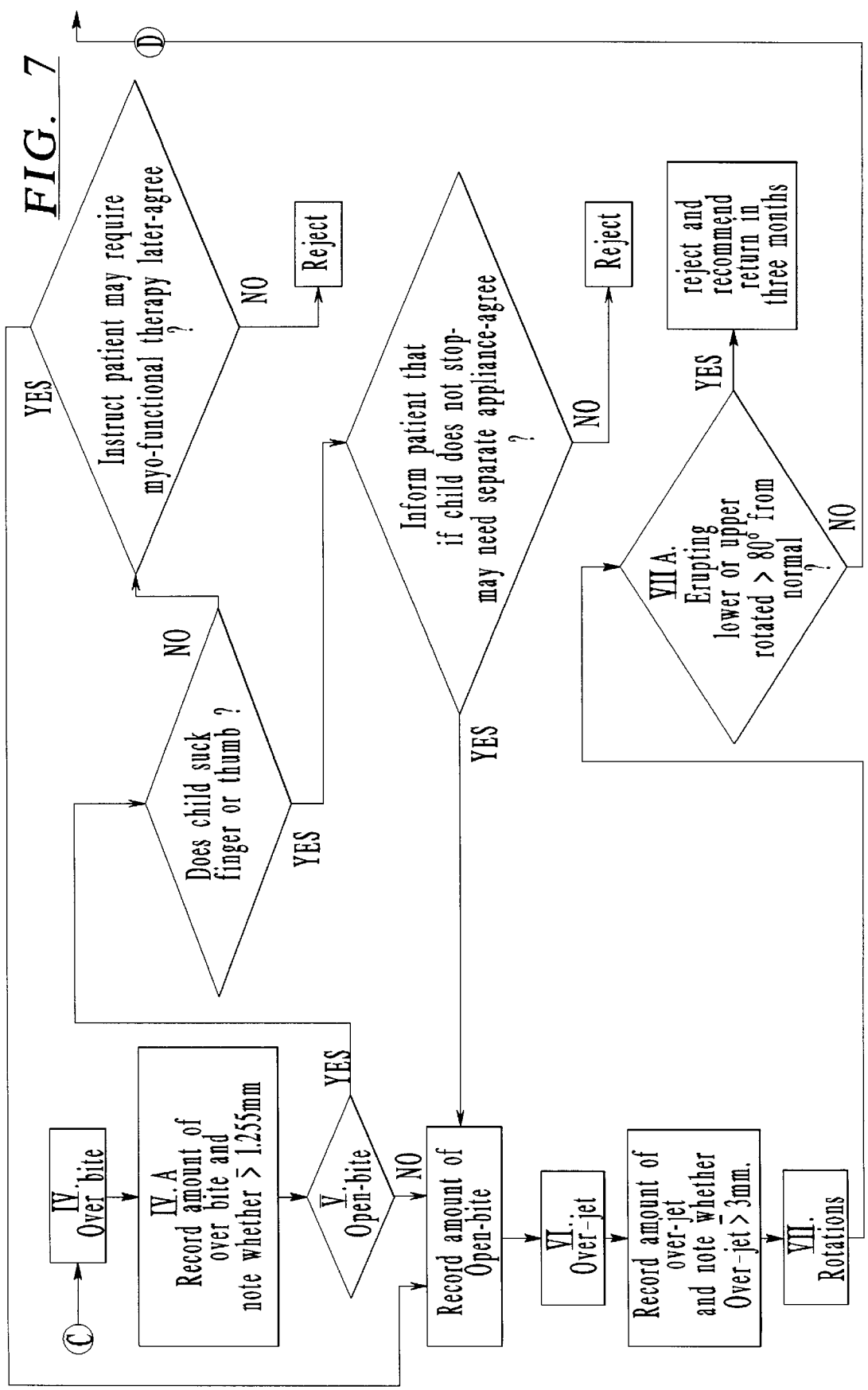
Figure 8:
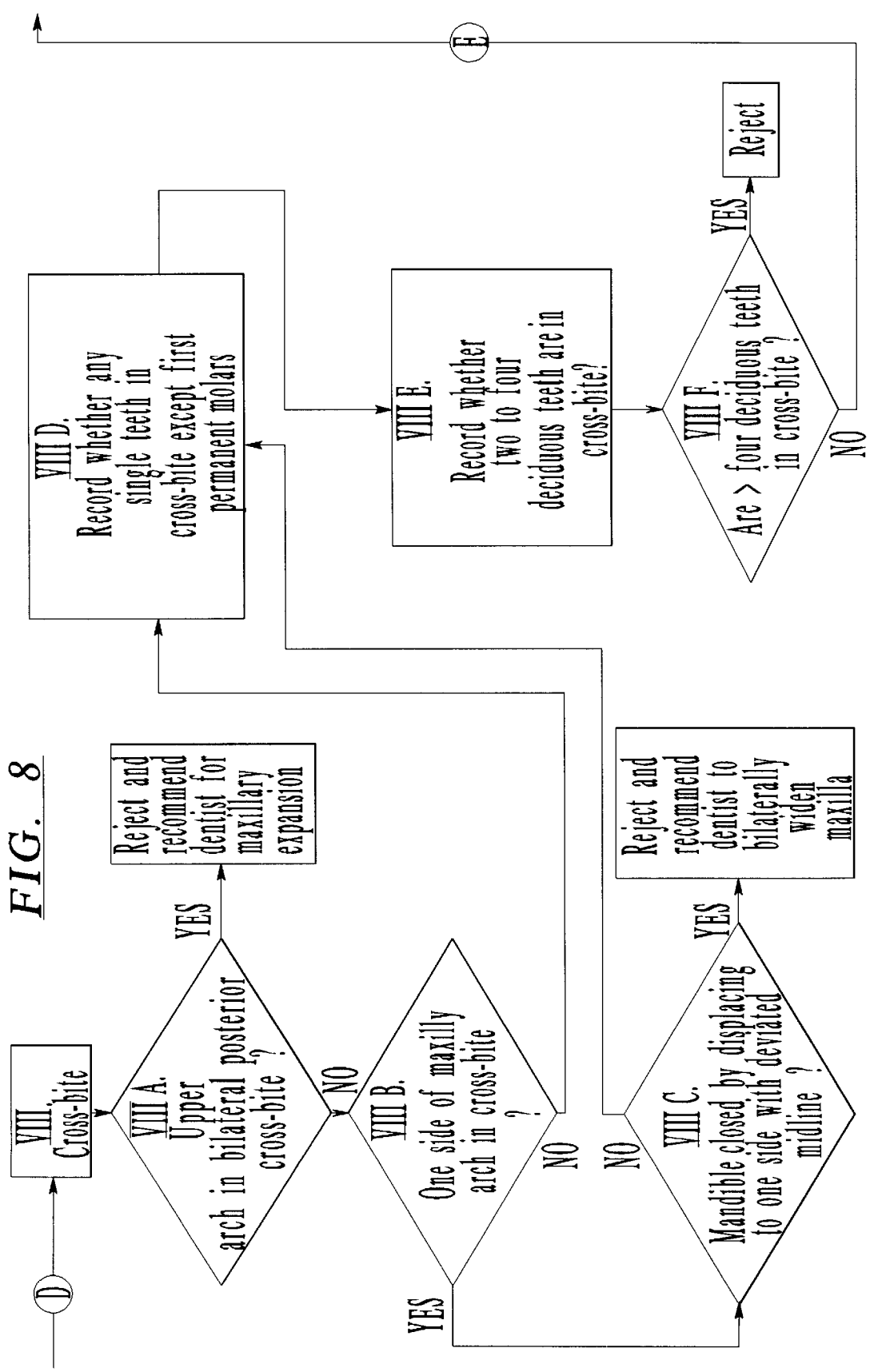
Figure 9:
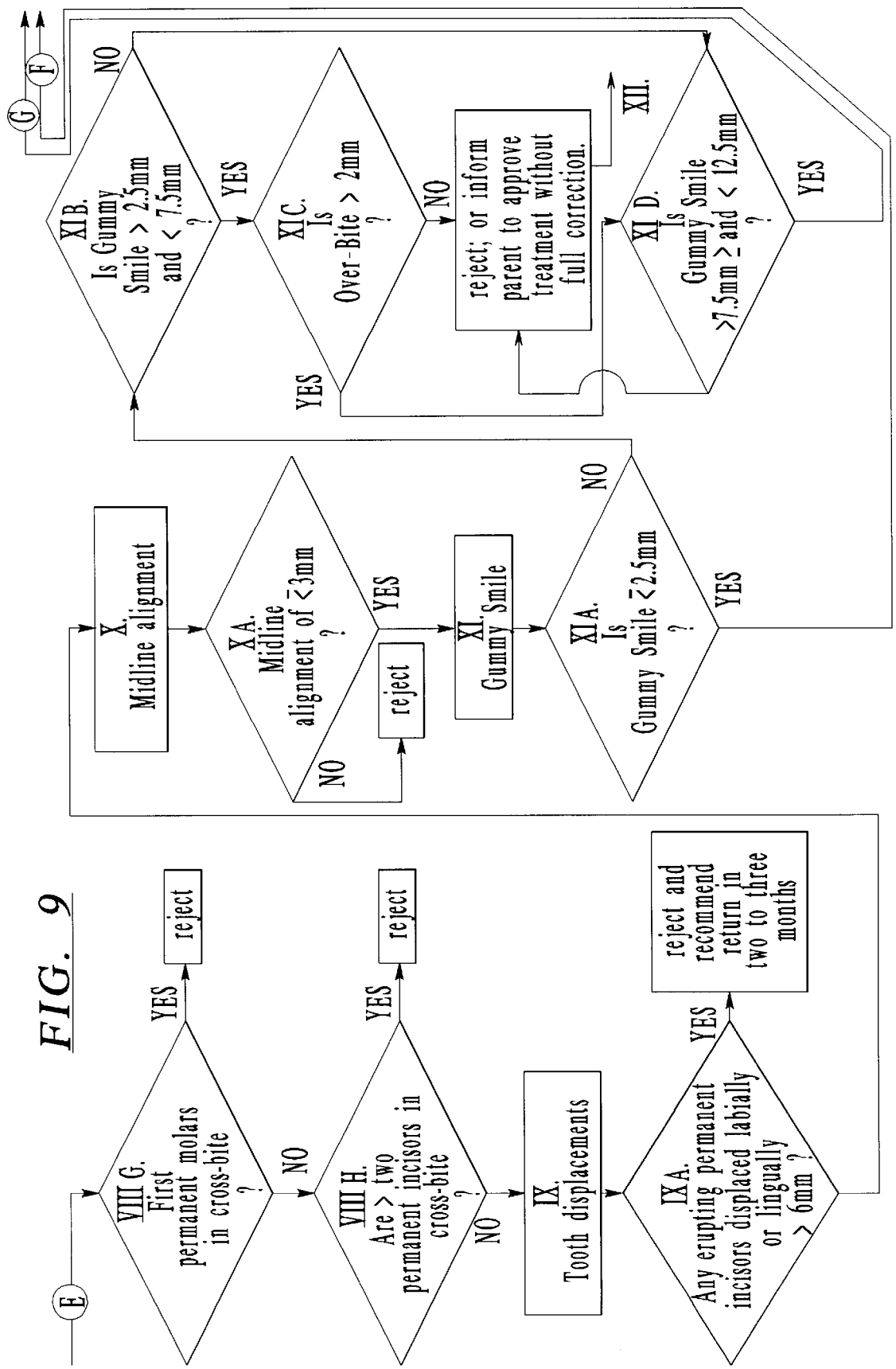
Figure 10:
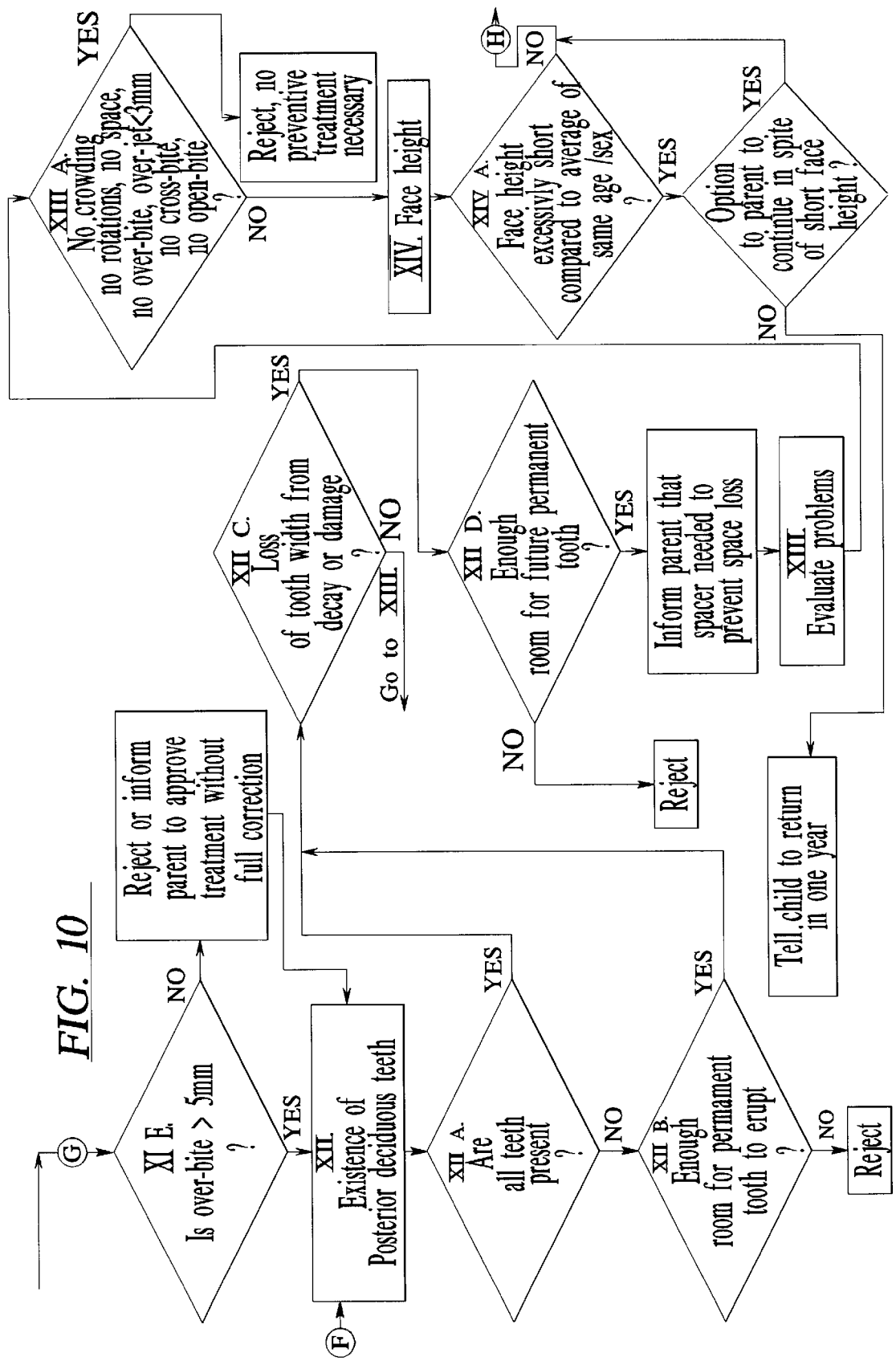
Figure 11:
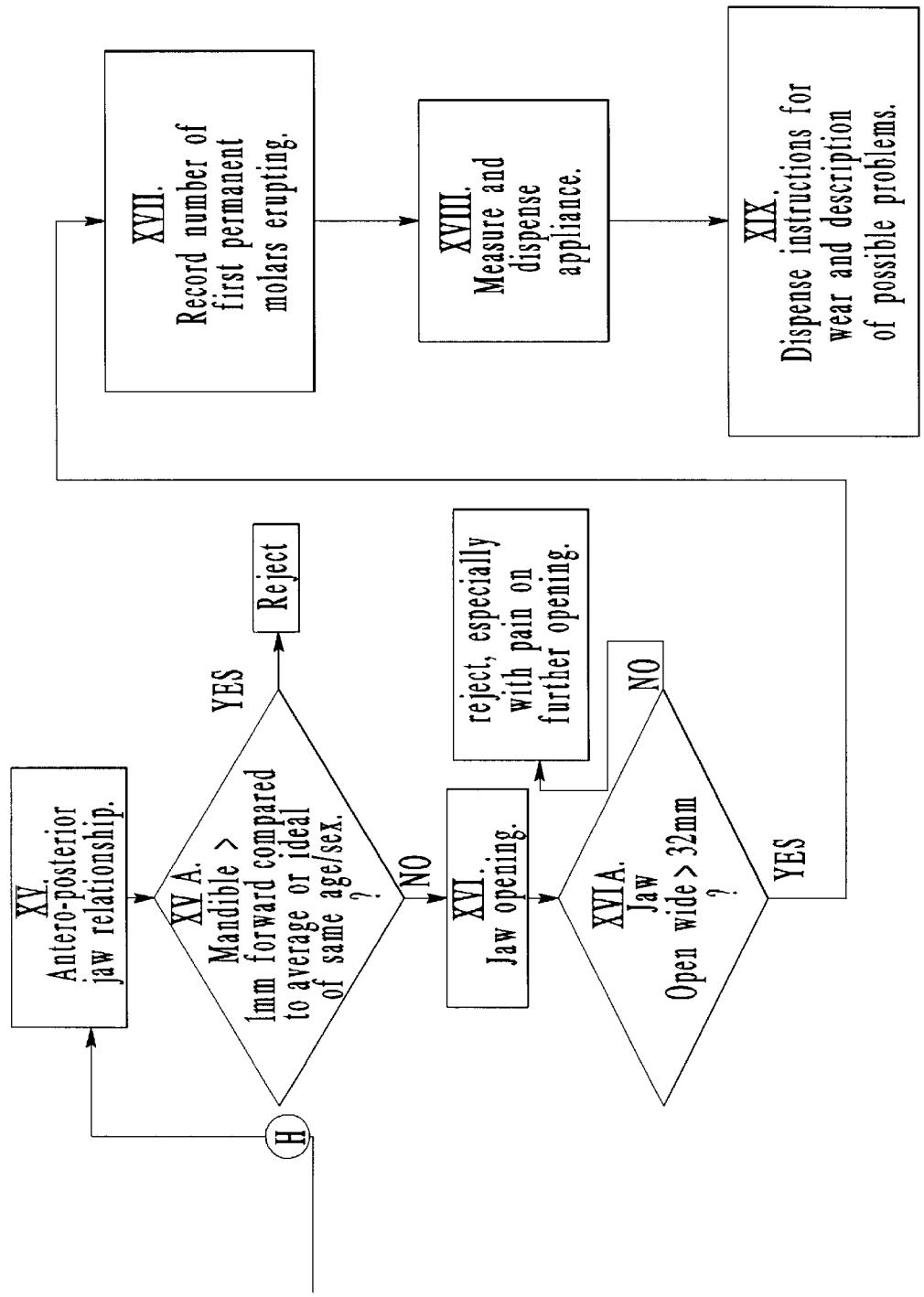

Referring now to FIG. 4, the first step, in the diagnosis is to determine the presence of deciduous and permanent incisors within the mouth of the individual as indicated by Step I of Program X.

Step I A is to determine whether all lower incisors are deciduous teeth or whether one or more of the lower incisors is a permanent tooth. If all lower incisors are deciduous the patient is rejected and provided instructions by the apparatus that they return when the first lower permanent incisor appears. If all four lower incisors are not deciduous teeth, the program proceeds to Step I B wherein the diagnostic apparatus determines whether other supernumerary teeth are present in the individual's mouth. If so, the patient is rejected outright for treatment if not, the program moves to Step I C. In Step I C the program determines how many of the lower incisors are permanent teeth. If one or two of the lower incisors are permanent, the program proceeds to Step II for lower arch length analysis. If three of the lower incisors are permanent, the program proceeds to Step I D and if all four lower incisors are permanent teeth, the program proceeds to Step I E.

In Step I D the program determines the amount of crowding which exists for the lone lower deciduous incisor. If the deciduous tooth is short of space by greater than 4 mm., the program will proceed then to Program Y and if the deciduous tooth is short of space by 4 mm. or less the program will proceed to Step II. In Step I E the program determines whether the four lower permanent incisors are crowded. If yes, the program will proceed to Program Y. If no, the program next continues to Step I F to determine how many upper incisors of the four are permanent teeth. If none of the upper incisors are permanent or if one or both of the upper central incisors are permanent, the program will proceed to Step II. If three or all of the upper incisors are permanent teeth, the program will then proceed to Program Y.

The next diagnosis Step II is, the diagnosis and measurement of the lower arch. The CODAD apparatus measures via the camera or cameras 42 one lower permanent central incisor, then multiplies that number by 4 and adds 1 mm. The CODAD apparatus further measures around the curvature of the arch from the mesial of one canine to the other and calculates the arch shortage or excess. This measurement is taken by having the patient place a special strip of paper across the upper central incisors. The cameras will then take a digital image of the mouth and teeth. The paper indicates to the electronics via digital data the size of the archas well as the size of all of the erupted and unerupted permanent teeth in the mouth.

The program first determines in Step II A if only one permanent lower central incisor is in and the space shortage is 7 mm or less. If the answer is no, the patient is rejected and if the answer is yes, the program proceeds to the next Step II B. In this step the program determines if both lower permanent central incisors are in and whether the shortage is 5.5 mm or less. If the answer is no, the patient is again rejected. If the answer is yes, the program proceeds to Step II C for determining whether there are three lower permanent incisors present and whether the shortage is 4.5 mm or less. If the answer is no, the patient is again rejected and if the answer is yes the program proceeds to Step II D. The program next determines in Step D the amount of arch space shortage or excess or whether a nil or zero shortage exists. The program simply records this fact and proceeds to whether there is excess space and records this fact and proceeds to Step III.

In Step III the program diagnoses arch length in the upper arch of the patient. The program calculates the size of the upper permanent incisors from the measured paper tape placed over the two upper central incisors and measures the arch size along the arc between the deciduous canines and calculates a shortage or excess. The program does so through utilizing all the digital images taken including front, lateral and upper occlusal video views.

In Step III A the program determines whether only one permanent central incisor is present and all the other upper incisors are deciduous and further determines whether the arch shortage is 7 mm or less. If the program determines yes to all these factors, it proceeds to Step III B. If the program determines no to any of these factors, the patient is rejected. In Step III B the program determines whether both upper permanent central incisors are present and the shortage is 5.5 mm or less. If the answer is yes, the program proceeds to Step III C and if the answer is no, the patient is again rejected for treatment. In Step III C the program determines whether three upper permanent incisors are present and the shortage is 4.5 mm or less. If the answer is yes, the program proceeds to Step III D and if the answer is no the patient is again rejected for treatment. If all four upper permanent incisors are present and fully erupted, the program will proceed to the CODAD Program Y. If not, the program simply proceeds to Step III E. In Step III E the program will determine the amount of shortage or excess or whether the shortage is nil or zero and simply record this fact and proceed to Step IV.

The next Step IV of the diagnosis determines the overbite condition for the patient utilizing the frontal and lateral views taken from the camera. In Step IV A, the program notes whether the overbite condition is 1.25 mm or greater in the patient, records the amount and proceeds to Step V. Table 1 illustrates a chart for the timing of overbite treatment for males and females. The chart indicates the latest age at which treatment can begin for a male and a female for a particular overbite condition. For example, an overbite correction requirement of 9.5 mm must be started in males at around the age of 9 years and 4 months and must be started in females at around the age of 4 years and 8 months in order to achieve full correction. Table I is used in both Programs X and Y. The information in the chart is an example of what is programmed into preprogrammed electronics 51 in order for apparatus 20 to conduct its appropriate diagnosis. Table 2 illustrates an overbite compensation chart for males and females of particular ages. The chart illustrates the amount of time necessary for a particular age that the individual must wear the appliance for full compensation of the overbite condition, and is most applicable to Program Y.

TABLE 1

GROWTH OF TIMING OF OVERBITE TREATMENT

| Correction Required (mm) | Male Oldest Age (CA) to Start Overbite Rx[1] Yrs Mos | Female Oldest Age (CA) to Start Overbite Rx[1] Yrs Mos |
| --- | --- | --- |
| 12.0 | 6 - 6 | |
| 11.5 | 6 - 11 | |
| 11.0 | 7 - 6 | |
| 10.5 | 8 - 1 | under 4 |
| 10.0 | 8 - 9 | 4 - 3 |
| 9.5 | 9 - 4 | 4 - 8 |
| 9.0 | 9 - 9 | 5 - 0 |
| 8.5 | 10 - 3 | 5 - 7 |
| 8.0 | 10 - 9 | 6 - 1 |
| 7.5 | 11 - 4 | 6 - 8 |
| 7.0 | 11 - 11 | 7 - 4 |
| 6.5 | 12 - 4 | 8 - 1 |
| 6.0 | 12 - 10 | 8 - 9 |
| 5.5 | 13 - 3 | 9 - 6 |
| 5.0 | 13 - 7 | 10 - 2 |
| 4.5 | 13 - 11 | 10 - 9 |
| 4.0 | 14 - 3 | 11 - 4 |
| 3.5 | 14 - 7 | 11 - 11 |
| 3.0 | 14 - 10 | 12 - 4 |

[1]Represented by remaining ANS-Me growth left from stated age to adulthood (19–9 Male, 21–0 Female).

TABLE 2

OVERBITE COMPENSATION (ANS—Me)[1]
REMAINING RETENTION AMOUNT & # YEARS/MONTHS FOR FULL COMPENSATION
Ideal retention usually requires half the time shown

| Rx During Year | | 1 Year[2] Active OG Rx | 1 mm. Yrs/Mos[3] | 2 mm. Yrs/Mos | 3 mm. Yrs/Mos | 4 mm. Yrs/Mos | 5 mm. Yrs/Mos | 6 mm. Yrs/Mos | 7 mm. Yrs/Mos | 8 mm. Yrs/Mos | 9 mm. Yrs/Mos | 10 mm. Yrs/Mos |
|---|---|---|---|---|---|---|---|---|---|---|---|---|
| 4-5 | M | 1.87 | 0-10 | 1-9 | 2-9 | 4-0 | 4-11 | 6-0 | 7-1 | 8-0 | 8-9 | 9-4 |
|  | F | 1.34 | 1-0 | 2-3 | 3-8 | 5-1 | 6-3 | 7-4 | 8-6 | 10-3 | — | — |
| 5-6 | M | 1.21 | 0-11 | 1-11 | 3-0 | 4-2 | 5-2 | 6-3 | 7-2 | 7-10 | 8-5 | 9-1 |
|  | F | 0.98 | 1-2 | 2-8 | 4-1 | 5-3 | 6-3 | 7-6 | 9-2 | 11-10 | — | — |
| 6-7 | M | 1.12 | 1-3 | 2-4 | 3-3 | 4-4 | 5-5 | 6-3 | 6-11 | 7-7 | 8-3 | 8-11 |
|  | F | 0.87 | 1-6 | 2-11 | 4-1 | 5-1 | 6-4 | 7-10 | 10-7 | — | — | — |
| 7-8 | M | 0.94 | 1-3 | 2-2 | 3-3 | 4-4 | 5-2 | 5-11 | 6-6 | 7-2 | 7-11 | 9-2 |
|  | F | 0.66 | 1-5 | 2-9 | 3-9 | 4-9 | 6-3 | 9-0 | — | — | — | — |
| 8-9 | M | 0.74 | 0-11 | 2-0 | 3-1 | 4-0 | 4-5 | 5-1 | 5-9 | 6-4 | 7-3 | 8-8 |
|  | F | 0.73 | 1-4 | 2-6 | 3-7 | 4-10 | 6-10 | — | — | — | — | — |
| 9-10 | M | 1.06 | 1-0 | 2-2 | 3-0 | 3-9 | 4-5 | 5-0 | 5-9 | 6-11 | — | — |
|  | F | 0.69 | 1-2 | 2-2 | 3-5 | 5-1 | 7-9 | — | — | — | — | — |
| 10-11 | M | 0.97 | 1-2 | 2-0 | 2-9 | 3-5 | 4-0 | 4-9 | 5-10 | — | — | — |
|  | F | 0.81 | 1-0 | 2-2 | 3-8 | 6-5 | — | — | — | — | — | — |
| 11-12 | M | 0.85 | 0-11 | 1-8 | 2-3 | 2-11 | 3-7 | 4-7 | — | — | — | — |
|  | F | 1.01 | 1-3 | 2-8 | 5-3 | — | — | — | — | — | — | — |
| 12-13 | M | 1.13 | 0-9 | 1-4 | 2-0 | 2-8 | 3-10 | — | — | — | — | — |
|  | F | 0.83 | 1-4 | 4-2 | — | — | — | — | — | — | — | — |
| 13-14 | M | 1.38 | 0-7 | 1-3 | 2-0 | 3-4 | — | — | — | — | — | — |
|  | F | 0.81 | 2-5 | — | — | — | — | — | — | — | — | — |
| 14-15 | M | 1.69 | 0-9 | 1-11 | — | — | — | — | — | — | — | — |
|  | F | 0.53 | 2-9 | — | — | — | — | — | — | — | — | — |
| 15-16 | M | 1.34 | 1-5 | — | — | — | — | — | — | — | — | — |
|  | F | 0.37 | — | — | — | — | — | — | — | — | — | — |
| 16-17 | M | 0.73 | — | — | — | — | — | — | — | — | — | — |
|  | F | 0.22 | — | — | — | — | — | — | — | — | — | — |
| 17-Adult | M | 0.67 | — | — | — | — | — | — | — | — | — | — |
|  | F | 0.56 | — | — | — | — | — | — | — | — | — | — |

[1]Based on actual figures (non-enlarged).
[2]Indicates ANS—Me growth for 1 year in mm.
[3]Indicates amount of ANS—Me growth stated in years & months beginning in the year following that stated in #2.
— = not compensated by adulthood.

The program in Step V determines the amount of open-bite present in the patient using again the frontal and lateral views taken from the camera. If the child has no open-bite, the machine simply records it and proceeds to Step VI. If there is an open-bite, the parent is asked if the child sucks their finger or thumb. If no, proceed to Step VI B. But the child may require some myofunctional therapy if the open-bite doesn't respond. If yes, proceed to Step VI, if not reject. If yes, the parent is informed that the child might require an anti-thumb sucking appliance in about 2 months. If the parent accepts this possibility, proceed to Step VI. If the parent rejects this idea, the patient is rejected.

The overjet condition in the patient is next diagnosed in Step VI and the program notes whether the overjet is 3 mm or greater. The program records the amount of overjet and proceeds to Step VII. Table 3 illustrates the timing of overjet treatment for males and females. The chart indicates the age at which treatment must begin for males and females to achieve a full correction of an overjet condition of a particular amount. For example, an overjet correction requirement of 9.5 mm. must begin in males at amount 9 years and 10 months and in females at about 7 years and 6 months to achieve full correction. Table 4 illustrates the amount of time that males and females must use the appliance in order to achieve full overjet compensation. The chart illustrates these figures for males and females at particular ages for a number of overjet conditions. Tables 3 and 4 are again most useful in Program Y.

TABLE 3

GROWTH OF TIMING OF OVERJET TREATMENT

| Correction Required (mm) | Male Oldest Age (CA) to Start Overjet Rx[1] Yrs Mos | Female Oldest Age (CA) to Start Overjet Rx[1] Yrs Mos |
|---|---|---|
| 12.0 | 7 - 4 | 5 - 3 |
| 11.5 | 7 - 11 | 5 - 6 |

TABLE 3-continued

GROWTH OF TIMING OF OVERJET TREATMENT

| Correction Required (mm) | Male Oldest Age (CA) to Start Overjet Rx[1] Yrs Mos | Female Oldest Age (CA) to Start Overjet Rx[1] Yrs Mos |
|---|---|---|
| 11.0 | 8 - 5 | 5 - 11 |
| 10.5 | 9 - 0 | 6 - 5 |
| 10.0 | 9 - 5 | 6 - 11 |
| 9.5 | 9 - 10 | 7 - 6 |
| 9.0 | 10 - 5 | 8 - 2 |
| 8.5 | 10 - 11 | 9 - 2 |
| 8.0 | 11 - 7 | 9 - 9 |
| 7.5 | 13 - 3 | 10 - 5 |
| 7.0 | 13 - 8 | 11 - 0 |
| 6.5 | 14 - 1 | 11 - 4 |
| 6.0 | 14 - 6 | 11 - 7 |
| 5.5 | 14 - 11 | 11 - 11 |
| 5.0 | 15 - 3 | 12 - 3 |
| 4.5 | 15 - 6 | 12 - 9 |
| 4.0 | 15 - 9 | 13 - 1 |
| 3.5 | 16 - 0 | 13 - 5 |
| 3.0 | 16 - 8 | 13 - 8 |

[1]Represented by remaining growth of mandible ART-GN plus inhibited maxillary growth ART-ANS for 1 year of active wear plus remaining years of adulthood figured on differences as in #2 (below) for retention (21–5 Male, 21–7 Female).
[2]Represented by difference of remaining growth of mandible ART-GN minus that of maxilla ART-NAS from stated age to adulthood (21–5 Male, 21–7 Female).

TABLE 4

OBJECT COMPENSATION (ANS—Me)[1]
REMAINING RETENTION AMOUNT & # YEARS/MONTHS FOR FULL COMPENSATION
Ideal retention usually requires half the time shown

| Rx During Year | | 1 Year[2] Active OG Rx | 1 Yr Other Funct. or Fixed Rx[3] | 1 mm. Yrs/Mos[4] | 2 mm. Yrs/Mos | 3 mm. Yrs/Mos | 4 mm. Yrs/Mos | 5 mm. Yrs/Mos | 6 mm. Yrs/Mos | 7 mm. Yrs/Mos | 8 mm. Yrs/Mos | 9 mm. Yrs/Mos | 10 mm. Yrs/Mos |
|---|---|---|---|---|---|---|---|---|---|---|---|---|---|
| 4-5 | M | 5.88 | 0.62 | 0-8 | 1-7 | 2-8 | 4-1 | 5-4 | 6-7 | 7-9 | 9-0 | 10-2 | 11-1 |
|  | F | 4.87 | 0.83 | 1-0 | 1-10 | 4-1 | 5-4 | 6-3 | 7-3 | 8-5 | 9-8 | 12-8 | — |
| 5-6 | M | 4.94 | 1.46 | 1-0 | 2-4 | 3-8 | 4-11 | 6-1 | 7-4 | 8-7 | 9-7 | 10-6 | 11-7 |
|  | F | 4.17 | 1.02 | 0-10 | 3-1 | 4-5 | 5-4 | 6-3 | 7-5 | 8-8 | 11-9 | — | — |
| 6-7 | M | 4.24 | 0.98 | 1-3 | 2-8 | 3-11 | 5-1 | 6-4 | 7-6 | 8-7 | 9-6 | 10-7 | — |
|  | F | 3.92 | 1.18 | 2-5 | 3-7 | 4-6 | 5-6 | 6-7 | 8-0 | 11-0 | — | — | — |
| 7-8 | M | 3.68 | 0.82 | 1-5 | 2-8 | 3-10 | 5-1 | 6-4 | 7-5 | 8-4 | 9-4 | — | — |
|  | F | 3.56 | 0.46 | 2-1 | 3-0 | 3-11 | 5-0 | 6-1 | 8-8 | — | — | — | — |
| 8-9 | M | 3.53 | 0.65 | 1-3 | 2-5 | 3-8 | 4-11 | 6-1 | 7-0 | 8-0 | 9-0 | — | — |
|  | F | 2.90 | 0.28 | 1-4 | 2-3 | 3-2 | 4-4 | 5-7 | 8-7 | — | — | — | — |
| 9-10 | M | 3.34 | 0.80 | 1-2 | 2-5 | 3-8 | 4-11 | 5-9 | 6-9 | 7-10 | — | — | — |
|  | F | 3.13 | 0.67 | 0-11 | 1-10 | 3-0 | 4-0 | 6-2 | — | — | — | — | — |
| 10-11 | M | 3.03 | 0.83 | 1-2 | 2-5 | 3-8 | 4-8 | 5-7 | 6-8 | — | — | — | — |
|  | F | 3.37 | 1.07 | 0-11 | 2-1 | 3-2 | 5-11 | — | — | — | — | — | — |
| 11-12 | M | 2.95 | 0.83 | 1-3 | 2-6 | 3-6 | 4-5 | 5-6 | — | — | — | — | — |
|  | F | 3.70 | 1.12 | 1-2 | 2-4 | 5-3 | — | — | — | — | — | — | — |
| 12-13 | M | 3.07 | 0.83 | 1-3 | 2-4 | 3-3 | 4-4 | — | — | — | — | — | — |
|  | F | 2.80 | 0.84 | 1-1 | 3-6 | — | — | — | — | — | — | — | — |
| 13-14 | M | 4.60 | 0.78 | 1-2 | 2-0 | 3-1 | — | — | — | — | — | — | — |
|  | F | 2.67 | 0.95 | 2-0 | — | — | — | — | — | — | — | — | — |
| 14-15 | M | 5.16 | 0.82 | 0-10 | 1-11 | 2-11 | — | — | — | — | — | — | — |
|  | F | 1.51 | 0.63 | 3-0 | — | — | — | — | — | — | — | — | — |
| 15-16 | M | 3.52 | 1.16 | 1-1 | 2-0 | — | — | — | — | — | — | — | — |
|  | F | 0.95 | 0.37 | — | — | — | — | — | — | — | — | — | — |
|  | M | 2.55 | 0.95 | 1-0 | — | — | — | — | — | — | — | — | — |

TABLE 4-continued

OBJECT COMPENSATION (ANS—Me)[1]
REMAINING RETENTION AMOUNT & # YEARS/MONTHS FOR FULL COMPENSATION
Ideal retention usually requires half the time shown

| Rx During Year | 1 Year[2] Active OG Rx | 1 Yr Other Funct. or Fixed Rx[3] | 1 mm. Yrs/Mos[4] | 2 mm. Yrs/Mos | 3 mm. Yrs/Mos | 4 mm. Yrs/Mos | 5 mm. Yrs/Mos | 6 mm. Yrs/Mos | 7 mm. Yrs/Mos | 8 mm. Yrs/Mos | 9 mm. Yrs/Mos | 10 mm. Yrs/Mos |
|---|---|---|---|---|---|---|---|---|---|---|---|---|
| 16-17 | | | | | | | | | | | | |
| F | 0.44 | 0.10 | — | — | — | — | — | — | — | — | — | — |
| M | 2.78 | 0.96 | — | — | — | — | — | — | — | — | — | — |
| 17-Adult | | | | | | | | | | | | |
| F | 0.75 | 0.45 | — | — | — | — | — | — | — | — | — | — |

[1]Based on actual figures (non-enlarged).
[2]Indicates ART—ANS plus ART—Gn growth in mm. for 1 yr. or OG and activator.
[3]Indicates ART—Gn minus ART—ANS growth in mm. for 1 yr. for Bionator, Frankel and other similar functions.
[4]Indicates ART—Gn minus ART—ANS stated in yrs. & mos. beginning in the year following that stated in #2 & #3.
— = not compensated by adulthood.

In Step VII, the tooth rotations using the upper and lower occlusal views from the camera are determined and diagnosed. The program first determines whether any erupting lower or upper incisors are rotated more than 80° from their ideal condition. If so, the patient is rejected and dispensed a recommendation to return in three months for another analysis. If less than 80°, the program proceeds to Step VIII.

The cross-bite condition of the patient is next diagnosed in Step VIII via the frontal and lateral views. In Step VIII A the program determines whether the upper arch is in a bilateral posterior cross-bite. If yes, the patient is rejected for treatment and dispensed a recommendation to see a dentist to perform a maxillary expansion prior to returning for further treatment by the CODAD apparatus.

If the answer is no, the program proceeds to Step VIII B and next diagnoses whether one side of the maxillary arch is in cross-bite. If the answer is no, the program will proceed to Step VIII D described below. If the answer is yes, the program will proceed to Step VIII C.

The program next diagnoses in Step VIII C whether the mandible or jaw closes by displacement to one side with a deviated midline which is determined from the frontal view and closure from open to close views from the camera. If yes, the patient is rejected for treatment at this time and referred to a dentist to bilaterally widen the maxilla prior to returning for further treatment via the CODAD apparatus. If no the program proceeds to Step VIII D and diagnoses whether any single tooth is in cross-bite with the exception of any first permanent molars. The program simply records this fact and proceeds to Step VIII E.

The program next records whether there are two, three or four deciduous teeth in cross-bite and proceeds to Step VIII F. The program then determines whether there are more than four deciduous teeth in cross-bite. If the answer is yes, the patient is rejected for further treatment. If the answer is no the program proceeds to Step VIII G. The diagnosis of Step G is to determine whether the first permanent molars are in cross-bite. If the answer is yes the patient is rejected for treatment and if the answer is no the program proceeds to Step VIII H. In this step the patient is diagnosed as to whether there are more than two permanent incisors in cross-bite and if so, the patient is rejected for treatment. If not, the program proceeds to Step IX.

The CODAD Program X uses the upper and lower occlusal views from the cameras to determine tooth displacement for Step IX. The program first determines whether there are any incoming permanent incisors displaced either labially or lingually by more than 6 mm in Step IX A. If yes, the patient is rejected and dispensed a recommendation to return in two to three months for a further analysis. If the answer is no the program proceeds to Step X. In this step the program determines the midline alignment of the upper and lower teeth using the frontal full facial view and the frontal intra-oral video views. If in Step X A the midline is off by 3 mm or less the program proceeds to Step XI and if the midline is off by more than 3 mm the patient is rejected for treatment.

In Step XI, the patient is diagnosed for a gummy smile condition using the frontal face video view with the patient smiling and frontal intra-oral video view. In Step XI A the program determines whether the gummy smile is 2.5 mm or less in the patient. If so, the program proceeds to Step XII described below. If no the program proceeds to Step XI B. In Step XI B the program determines whether the gummy smile is between 2.5 mm and 7.5 mm. If yes, the program proceeds to Step XI C and if no, the program proceeds to Step XI D. In Step XI C the program compares the gummy smile to the patient's overbite condition and whether this overbite condition is in excess of 2 mm. If so, the program proceeds to Step XI D and if not, the patient is given the option of being either rejected for treatment or continuing with diagnosis and treatment upon approval that the gummy smile condition cannot be fully corrected.

In Step XI D the program diagnoses whether the gummy smile is between 7.5 mm and 12.5 mm. If the answer is yes the program proceeds to Step XI E and if the answer is no the patient is again given the option to continue without full correction or be rejected for further treatment. In Step E the program diagnoses whether the patient's overbite is greater than 5 mm. If yes the program proceeds to Step XII and if no the patient is again given the option of continuing without full correction of gummy smile or being rejected for treatment.

The diagnosis Program X in Step XII determines the presence or absence of posterior deciduous teeth in the patient using the lateral intra-oral and upper and lower occlusal views. This determination includes determining whether the deciduous canines are present or absent. In Step XII A the diagnostic Program X determines whether all of the patients teeth are present and whether there is any loss of tooth width from external damage or decay. In Step XII A the program first determines whether all of the patient's teeth are present. If yes, the program proceeds to Step XII C and if no, the program proceeds to Step XII B. In Step XII B the diagnostic program determines whether there is enough room for the permanent tooth to come in and replace the missing teeth of the patient. If no, the patient is rejected for further treatment. If yes, the program again proceeds to Step XII C. In this step, the program next determines if there is any loss of tooth width for one or more teeth from damage or decay. If so, the program continues to Step XII D and if not the program continues to Step XII. In Step XII D the program next diagnoses whether there is enough room for a future tooth to erupt in the damaged or decayed area. If not, the patient is rejected for treatment and if so the program continues to Step XIII.

If the patient had some damage or decay to one or more teeth but the program determines that there is enough room for the future permanent teeth to erupt, the diagnosis will continue for the patient. However, the apparatus 20 will dispense information to the patient instructing them that a spacer should be obtained and placed within the gap or gaps to prevent further loss of space in the damaged area. Whether this is done will determine whether the patient can achieve full correction.

In Step C, the program diagnoses whether there are any missing teeth and further whether there is sufficient room for the erupting permanent tooth that replaces the missing deciduous tooth. If the answer is yes, the program proceeds to Step XIII but dispenses information to the patient that a spacer should be obtained and placed within the gap to prevent further space loss. If the answer is no, the patient is rejected for treatment.

In Step XIII the program conducts a recap or summary of all the conditions diagnosed to this point in the diagnosis procedure. In Step XIII A, the program compiles and analyzes the information to determine the condition of the patient's teeth and if no crowding, no rotations, no spaces, no overbite, overjet of less than 3 mm, no cross-bites, and no open-bites are present in the patient, the program notifies the patient that no preventive treatment is necessary. If the program determines that one or more of the above conditions is not met, the program continues to Step XIV.

The apparatus utilizes the frontal and lateral face views taken from the cameras and the Program Step XIV determines the face height of the individual. In Step XIV A the program diagnoses whether the face height of the patient is excessively short compared to preprogrammed standards or median face height of individuals of similar age and sex. If the face height is not excessively short for a person of the same age and sex, the program proceeds to Step XIV B. If the patient's face height is excessively short, the patient is notified and if the patient wants to proceed, the program continues to Step XV. If no, then the patient is rejected. The parent is instructed to bring child back in 6 months to one year after the permanent teeth are fully erupted.

Tables 5 and 6 illustrate for males and females, respectively, the average face height characteristics for direct radiographic readings. Tables 5 and 6 illustrate the mean face height for males and females of various ages from four to twenty-one. These tables further provide standard deviation information beyond the mean face height for the various ages and also provides projected growth information both to full adulthood and for each upcoming year. As with the information in Tables 1–4, this information may be programmed into the diagnostic preprogrammable electronics in order that the diagnoses may take this information into account as described above and under Program Y.

TABLE 5

MALE TOTAL ANTERIOR FACE HEIGHT (N-Me) FOR DIRECT RADIOGRAPHIC READINGS

| CA Yrs. | Mean mm. | S.D. | Human Limits ± 3 S.D. mm. | Abnormal Limits ± 2 S.D. mm. | Ideal Funct. Appl Limits mm. | Funct.* Appl. Contraindication above mm. | % Total Growth Completed | Total* Growth Left to Adult mm. | Expected* Growth Next Year mm. |
|---|---|---|---|---|---|---|---|---|---|
| 4 | 93.7 | 4.10 | 81.4 to 106.0 | 85.5 to 101.9 | 81.4 to 101.9 | 102.0 | 73.39% | 33.99 (31.30) | 3.58 (3.51) |
| 5 | 97.3 | 3.79 | 85.9 to 108.7 | 89.7 to 104.9 | 85.9 to 104.9 | 105.0 | 76.19% | 30.41 (27.79) | 3.18 (2.73) |
| 6 | 100.5 | 4.14 | 88.1 to 112.9 | 92.2 to 108.8 | 88.1 to 108.8 | 108.9 | 78.68% | 27.23 (25.07) | 2.57 (2.41) |
| 7 | 103.1 | 4.16 | 90.6 to 115.5 | 94.7 to 111.4 | 90.6 to 111.5 | 111.5 | 80.69% | 24.66 (22.65) | 2.44 (2.22) |
| 8 | 105.5 | 4.33 | 92.5 to 118.5 | 96.8 to 114.1 | 92.5 to 114.1 | 114.2 | 82.60% | 22.22 (20.43) | 2.03 (1.84) |
| 9 | 107.5 | 4.30 | 94.6 to 120.4 | 98.9 to 116.1 | 94.6 to 116.1 | 116.2 | 84.19% | 20.19 (18.59) | 2.42 (2.28) |
| 10 | 109.9 | 4.46 | 96.6 to 123.3 | 101.0 to 118.9 | 96.6 to 118.9 | 119.0 | 86.09% | 17.77 (16.31) | 2.25 (2.07) |
| 11 | 112.2 | 4.83 | 97.7 to 126.7 | 102.5 to 121.9 | 97.7 to 121.9 | 122.0 | 87.86% | 15.52 (14.24) | 2.05 (1.81) |
| 12 | 114.2 | 4.97 | 99.3 to 129.2 | 104.3 to 124.2 | 99.3 to 124.2 | 124.3 | 89.43% | 13.47 (12.43) | 2.14 (2.01) |
| 13 | 116.4 | 5.40 | 100.2 | 105.6 | 100.2 | 127.3 | 91.15% | 11.33 | 2.92 |

TABLE 5-continued

MALE TOTAL ANTERIOR FACE HEIGHT (N-Me) FOR DIRECT RADIOGRAPHIC READINGS

| CA Yrs. | Mean mm. | S.D. | Human Limits ± 3 S.D. mm. | Abnormal Limits ± 2 S.D. mm. | Ideal Funct. Appl Limits mm. | Funct.* Appl. Contraindication above mm. | % Total Growth Completed | Total* Growth Left to Adult mm. | Expected* Growth Next Year mm. |
|---|---|---|---|---|---|---|---|---|---|
| | | | to 132.6 | to 127.2 | to 127.2 | | | (10.42) | (2.7) |
| 14 | 119.3 | 6.24 | 100.6 to 138.0 | 106.8 to 131.8 | 100.6 to 131.8 | 131.9 | 93.42% | 8.41 (7.72) | 3.23 (2.95) |
| 15 | 122.5 | 6.10 | 104.2 to 140.8 | 110.3 to 134.7 | 104.2 to 134.7 | 134.8 | 95.93% | 5.18 (4.78) | 2.96 (2.06) |
| 16 | 124.8 | 5.63 | 107.0 to 141.7 | 113.9 to 136.0 | 107.9 to 136.0 | 136.1 | 97.73% | 2.94 (2.72) | 2.21 (1.33) |
| 17 | 126.2 | 5.48 | 109.8 to 142.7 | 115.2 to 137.2 | 109.8 to 137.2 | 137.3 | 98.82% | 1.51 (1.39) | 1.43 (1.38) |
| 21.1 | 127.7 | 5.85 | 110.2 to 145.3 | 116.0 to 139.4 | 110.2 to 139.4 | 139.5 | 100.0% | 0 | 0 |

*( ) represents the non-enlarged amount for actual growth increment.

TABLE 6

FEMALE TOTAL ANTERIOR FACE HEIGHT (N—Me) FOR DIRECT RADIOGRAPHIC READINGS

| CA Yrs. | Mean mm. | S.D. | Human Limits ± 3 S.D. mm. | Abnormal Limits ± 2 S.D. mm. | Ideal Funct. Appl Limits mm. | Funct.* Appl. Contraindication above mm. | % Total Growth Completed | Total* Growth Left to Adult mm. | Expected* Next Year mm. |
|---|---|---|---|---|---|---|---|---|---|
| 4 | 89.5 | 3.23 | 79.8 to 99.2 | 83.0 to 95.9 | 79.8 to 95.9 | 96.0 | 77.68% | 25.71 (23.77) | 3.62 (3.27) |
| 5 | 93.1 | 3.76 | 81.8 to 104.4 | 85.6 to 100.6 | 81.8 to 100.6 | 100.7 | 80.83% | 22.08 (20.50) | 3.15 (2.95) |
| 6 | 96.2 | 3.86 | 84.7 to 107.8 | 88.5 to 104.0 | 84.7 to 104.0 | 104.1 | 83.56% | 18.93 (17.55) | 2.18 (2.12) |
| 7 | 98.4 | 3.86 | 86.8 to 110.0 | 90.7 to 106.1 | 86.8 to 106.1 | 106.2 | 85.45% | 16.75 (15.44) | 2.00 (1.85) |
| 8 | 100.4 | 3.96 | 88.5 to 112.3 | 92.5 to 108.3 | 88.5 to 108.3 | 108.4 | 87.19% | 14.75 (13.59) | 2.14 (1.96) |
| 9 | 102.6 | 4.13 | 90.2 to 114.9 | 94.3 to 110.8 | 90.2 to 110.8 | 110.9 | 89.05% | 12.61 (11.63) | 2.05 (1.86) |
| 10 | 104.6 | 4.13 | 92.2 to 117.0 | 96.4 to 112.9 | 92.2 to 112.9 | 113.0 | 90.84% | 10.55 (9.77) | 1.96 (1.85) |
| 11 | 106.6 | 4.48 | 93.4 to 119.7 | 97.8 to 115.4 | 93.4 to 115.4 | 115.5 | 92.54% | 8.59 (7.92) | 2.08 (1.96) |
| 12 | 108.7 | 4.39 | 95.5 to 121.8 | 99.9 to 117.5 | 95.5 to 117.5 | 117.6 | 94.35% | 6.51 (5.96) | 1.97 (1.74) |
| 13 | 110.6 | 4.56 | 97.0 to 124.3 | 101.5 to 119.8 | 97.0 to 119.8 | 119.9 | 96.07% | 4.53 (4.22) | 1.55 (1.42) |
| 14 | 112.2 | 4.62 | 98.3 to 126.1 | 102.9 to 121.4 | 98.3 to 121.4 | 121.5 | 97.74% | 2.98 (2.81)(1.03) | 1.10 |
| 15 | 113.3 | 4.63 | 99.4 to 127.2 | 104.0 to 122.6 | 99.4 to 122.6 | 122.7 | 98.37% | 1.88 (1.77) | 0.71 (0.67) |
| 16 | 114.0 | 4.79 | 99.6 to 128.4 | 104.4 to 123.6 | 99.6 to 123.6 | 123.7 | 98.98% | 1.17 (1.11) | 0.46 (0.43) |
| 17 | 114.5 | 4.93 | 99.7 to | 104.6 to | 99.7 to | 124.4 | 99.38% | 0.71 (0.67) | 0.71 (0.67) |

TABLE 6-continued

FEMALE TOTAL ANTERIOR FACE HEIGHT (N—Me) FOR DIRECT RADIOGRAPHIC READINGS

| CA Yrs. | Mean mm. | S.D. | Human Limits ± 3 S.D. mm. | Abnormal Limits ± 2 S.D. mm. | Ideal Funct. Appl Limits mm. | Funct.* Appl. Contraindication above mm. | % Total Growth Completed | Total* Growth Left to Adult mm. | Expected* Next Year mm. |
|---|---|---|---|---|---|---|---|---|---|
| 20.7 | 115.2 | 4.99 | 129.2 100.2 to 130.2 | 124.3 105.2 to 125.2 | 124.3 100.2 to 125.2 | 125.3 | 100.0% | 0 | 0 |

*( ) represents the non-enlarged amount for actual growth increment.

The next Step XV A of the diagnosis determines whether the antero-posterior jaw relationship is forward by more than 1 mm relative to an ideal 1 mm short of an end-to-end incisal relationship. This is done by using the lateral face view and lateral intra-oral view from the cameras 42 of the machine. If no, the program proceeds to Step XVI and if yes, the patient is rejected for treatment. In Step XVI the program compares the jaw opening of the patient to that of an average or median patient of like age and sex. In Step XVI A, if the child's jaw opens to its widest position and the opening is 32 mm or less, the patient is rejected for treatment especially if the patient experiences pain when asked by the apparatus to further open the jaw. If not, the program proceeds to Step XVII. This step of the diagnosis determines and records the presence or absence of first permanent molars within the patient's mouth using the lateral and occlusal views from the cameras. The program determines whether at least two first permanent molars are erupting into the mouth, simply records this fact and proceeds to Step XVIII.

In Step XVIII the computer program of the CODAD apparatus 20 diagnoses the patient's condition based upon all of the previous steps and issues or dispenses a correct appliance for treating the patient. If necessary, a second appliance is also issued to the patient based upon predicted sizes of the teeth taken from the diagnosed and measured conditions of the patients mouth, and the appliance for example may be about 3 half sizes larger than the initial appliance. This is to allow the appliance to treat a crowding condition and allow the teeth to expand to their normal uncrowded condition.

The program then in Step XIX dispenses directions for use of the appliance or appliances to the patient and preferably, also includes a notification to the patient of a series of possible problems which may arise and require answers during treatment. These instructions may be detailed and include the amount of wear required for the full correction of the patients condition and when if necessary the patient should switch to a second appliance. The CODAD apparatus may be programmed to dispense only one appliance or more than one appliance depending upon the regional economic and social conditions in the area which the patient lives. For example, the apparatus may dispense only the appliance that will fit the final proper occlusion condition of the patient with complete instructions for its use. If the diagnosis determines that one or more deciduous posterior teeth must be removed from the patient's mouth, directions may be dispensed by the CODAD apparatus to the patient to visit a dentist so that the extraction is done at the right time. The patient may then be instructed to return for treatment via the apparatus of the invention.

The apparatus also dispenses instructions or information regarding particular limitations on the final occlusal correction the patient may expect based upon the diagnosis of their occlusal condition. These may include mentioning possible compromised treatment results based upon whether the patient sucks their thumb, is susceptible to or has a joint problem in the jaw, suffers from premature injuries to the teeth or mouth, or has missing teeth or other spaces that require maintenance.

The machine can also simply dispense a one-size fits-all appliance as well which does not need appropriate measures for many applications.

The second diagnostic Program Y is for males and females from about 7 years of age and older. The logic flowcharts for this program are illustrated in FIGS. 12–22 and are described below with reference to these FIGS.

Figure 12:
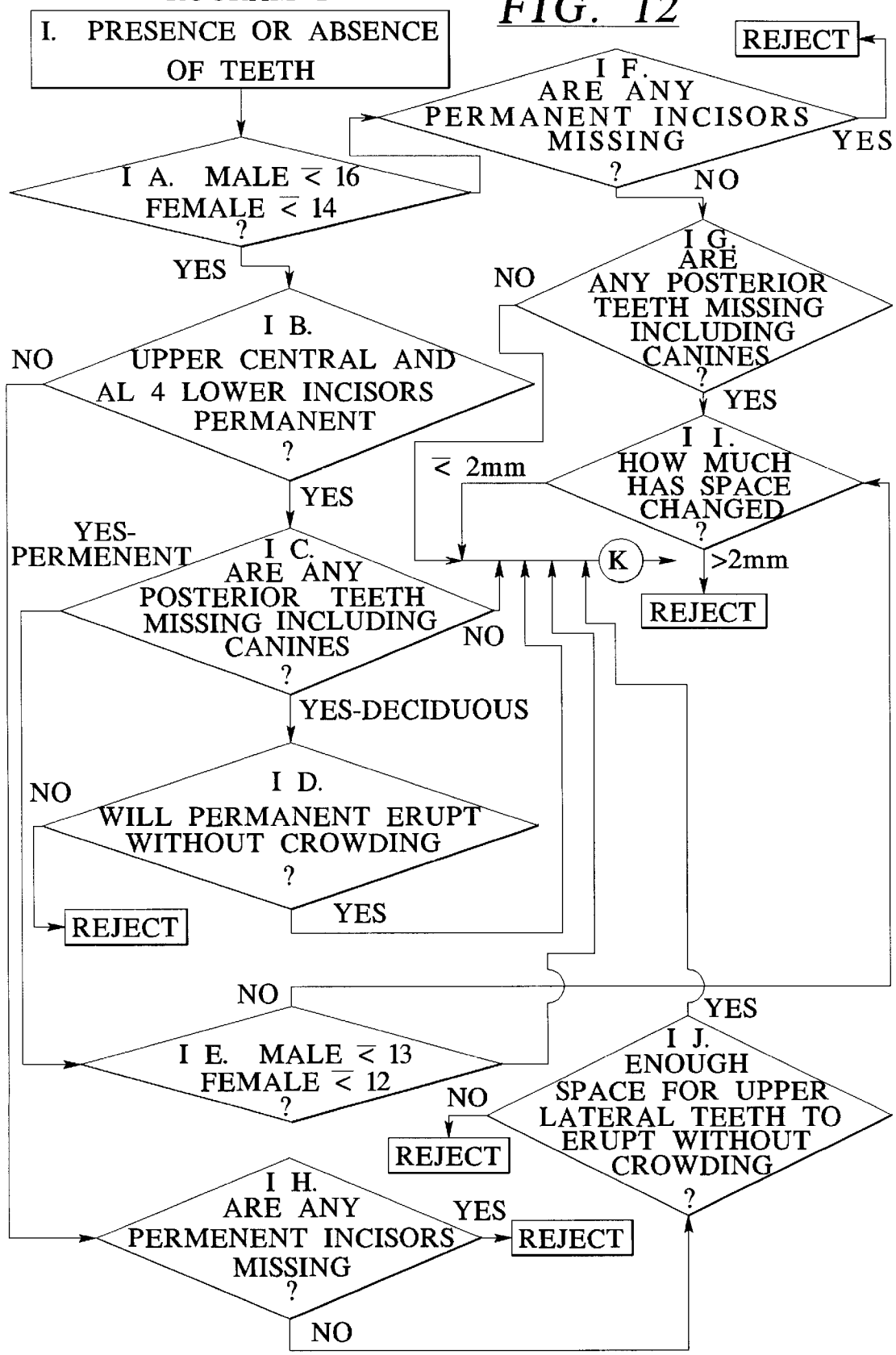
FIGS. 12–22 are a flowchart diagram of the diagnosis procedure for individuals in the age range of about 7 years old and up.
Figure 13:
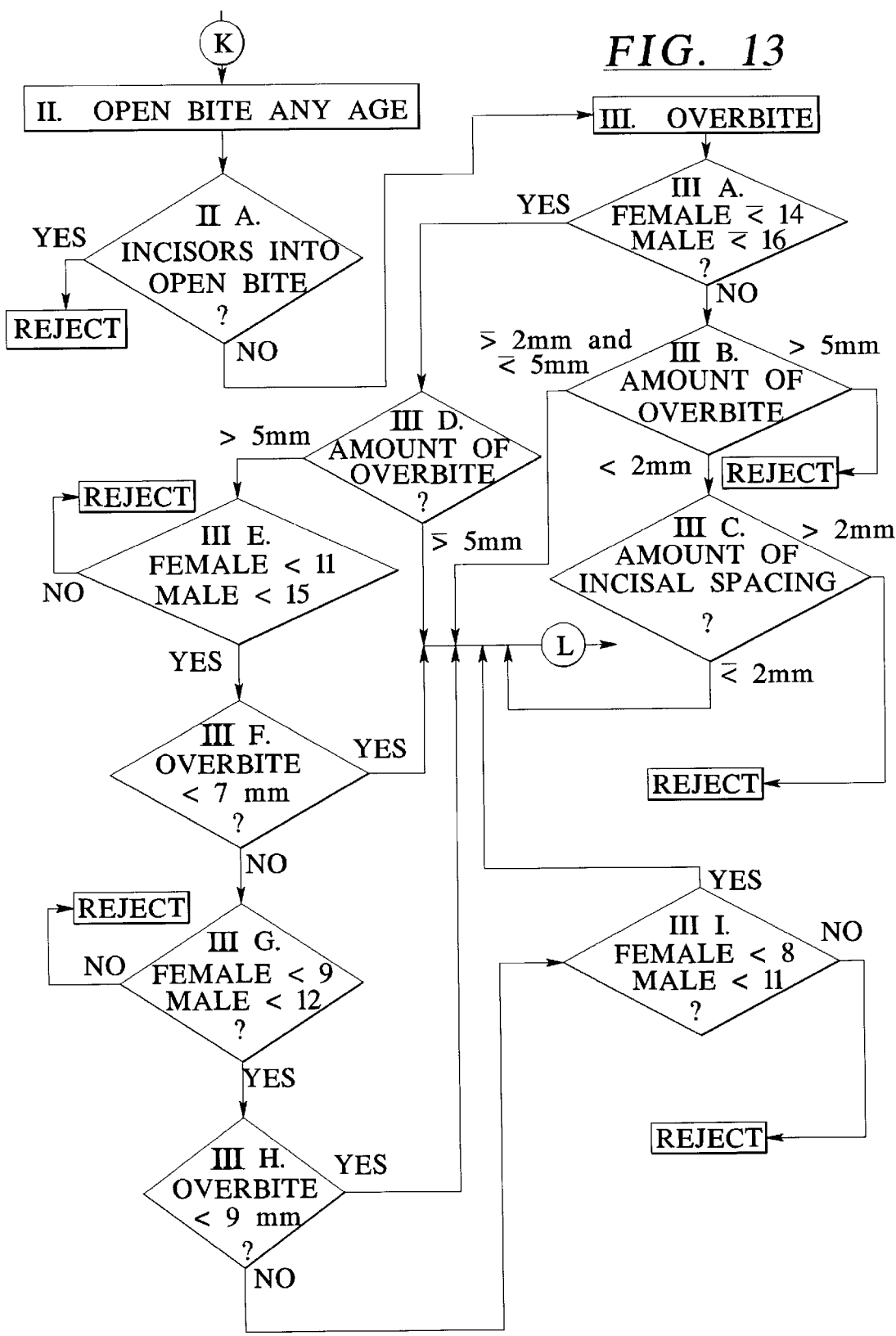
Figure 14:
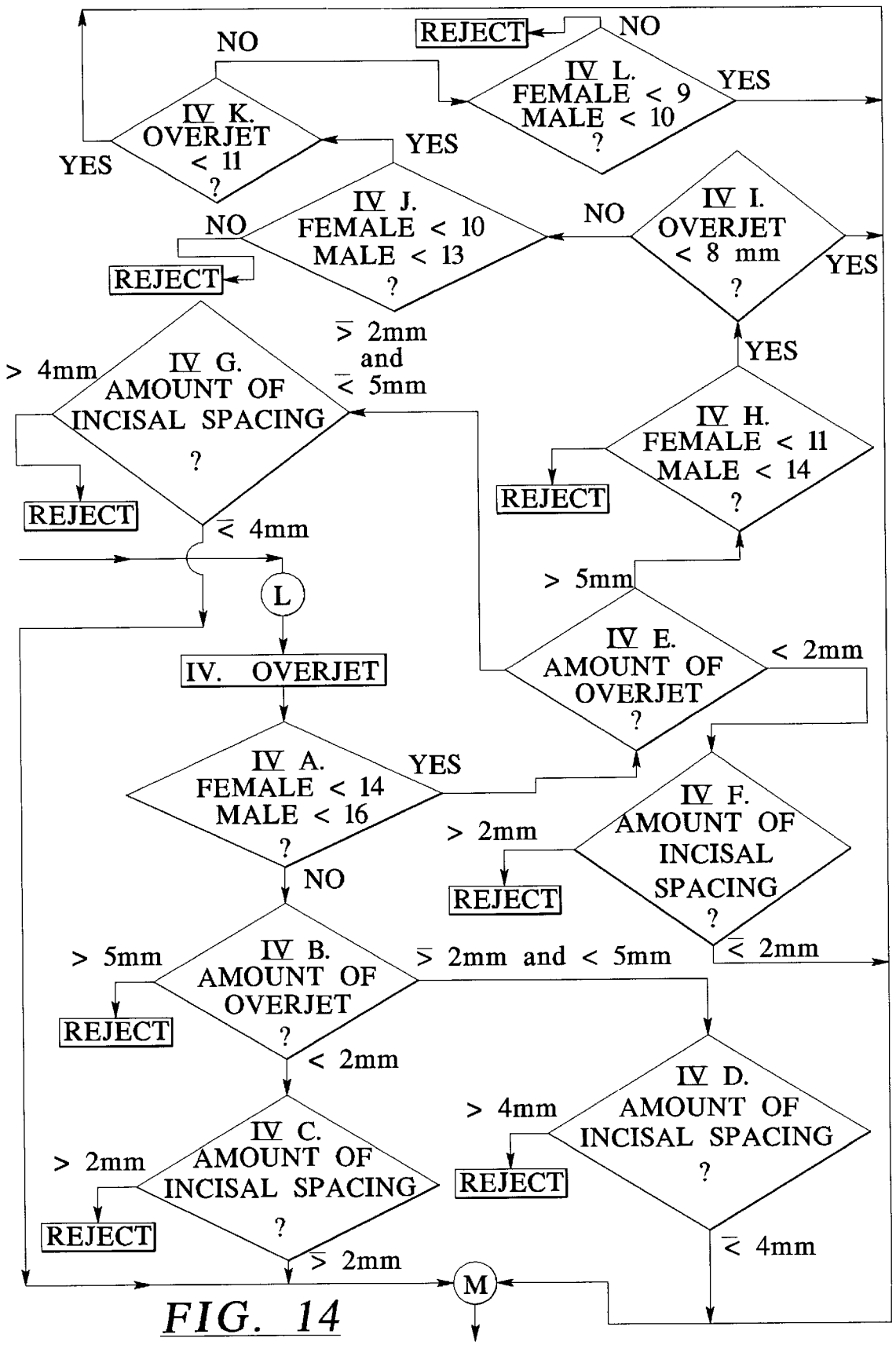
Figure 15:
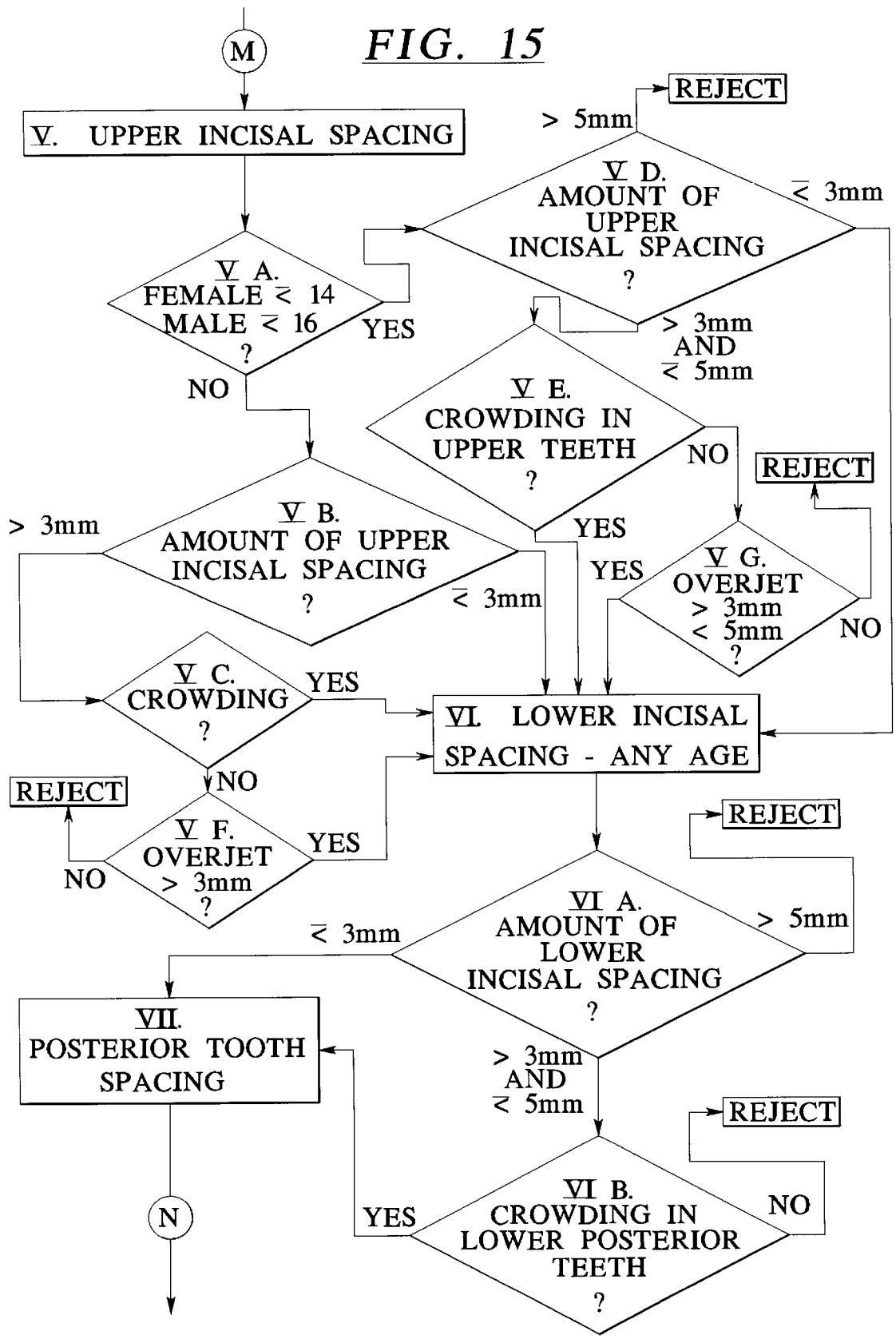
Figure 16:
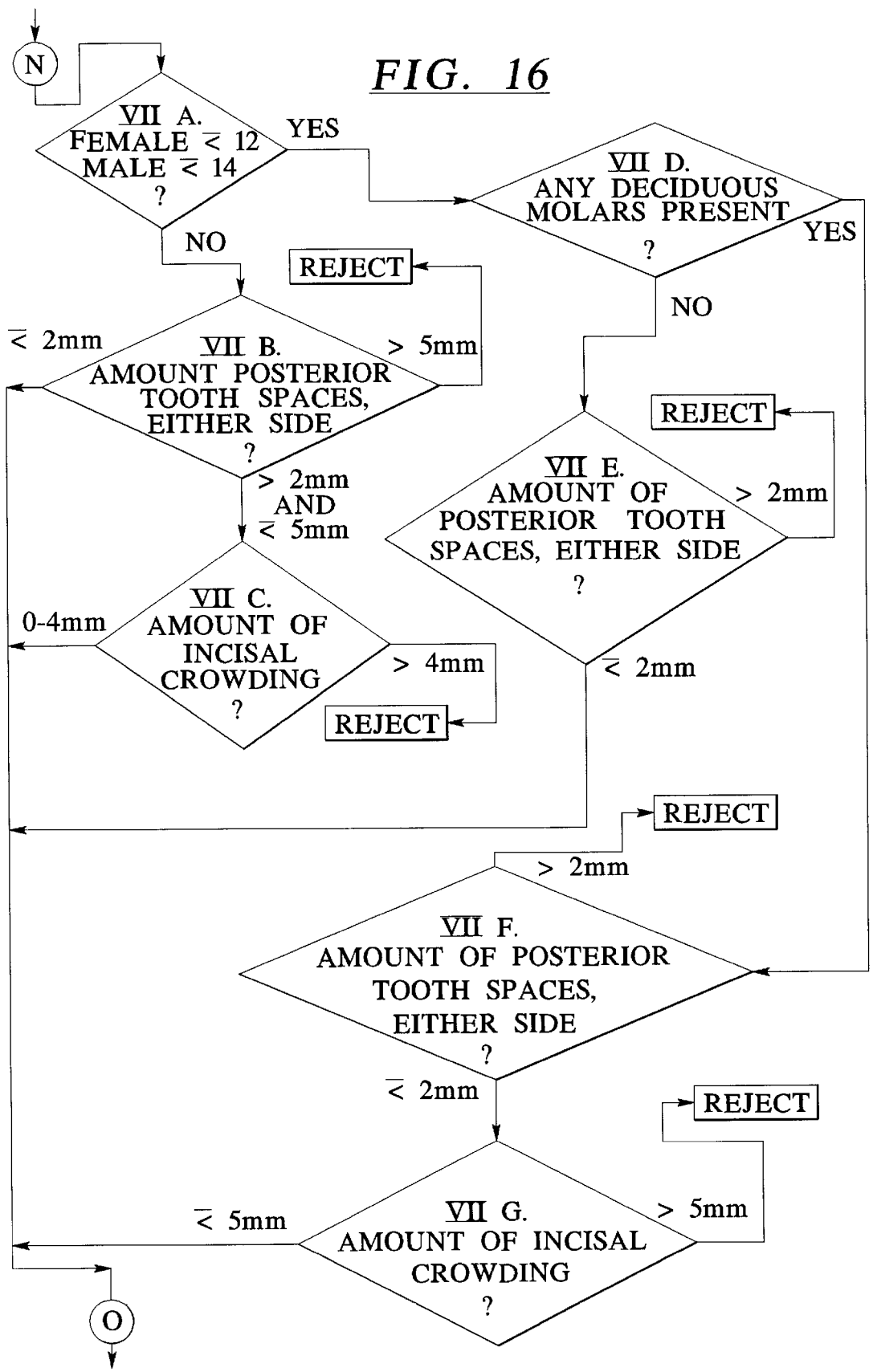
Figure 17:
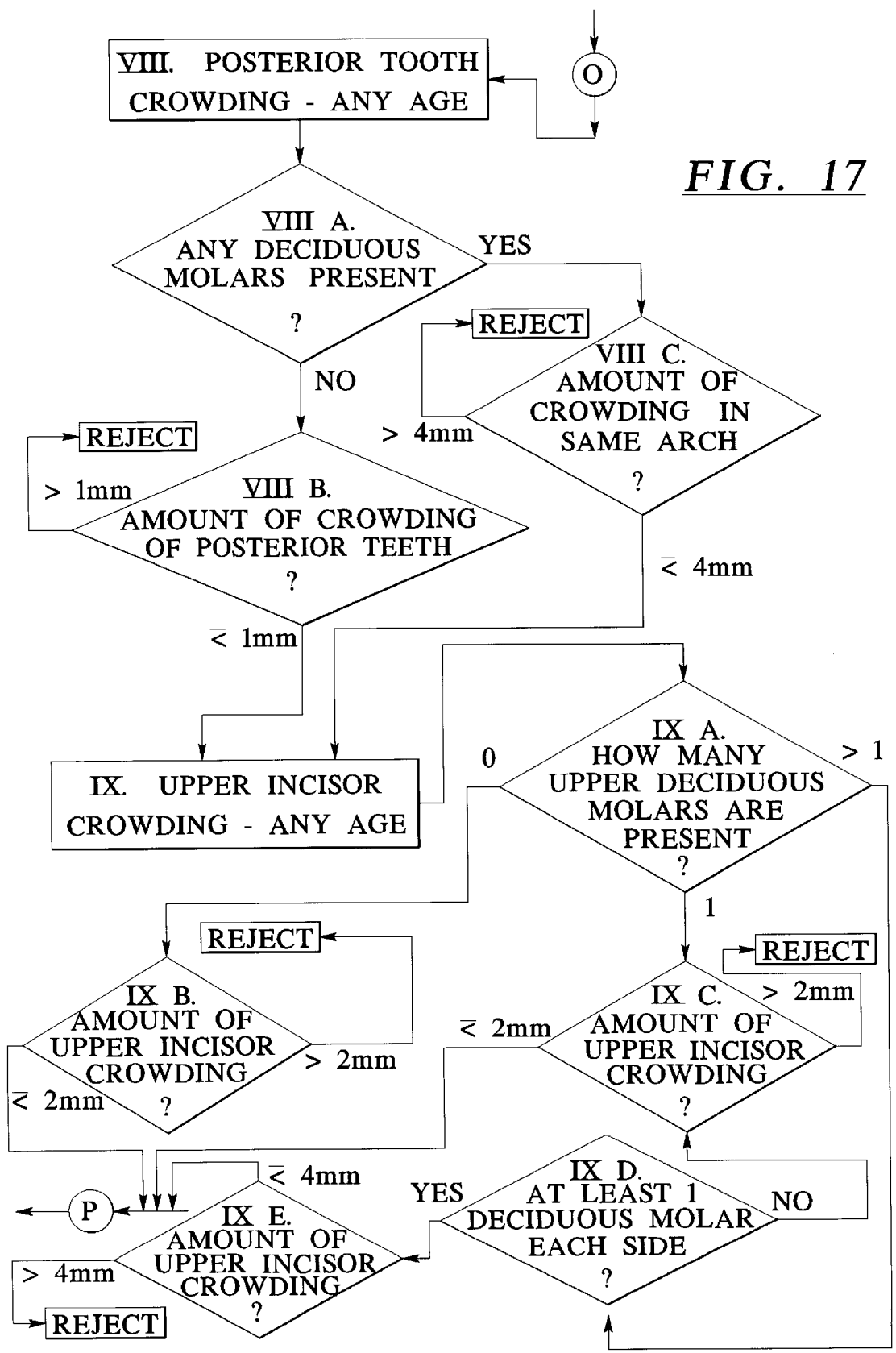
Figure 18:
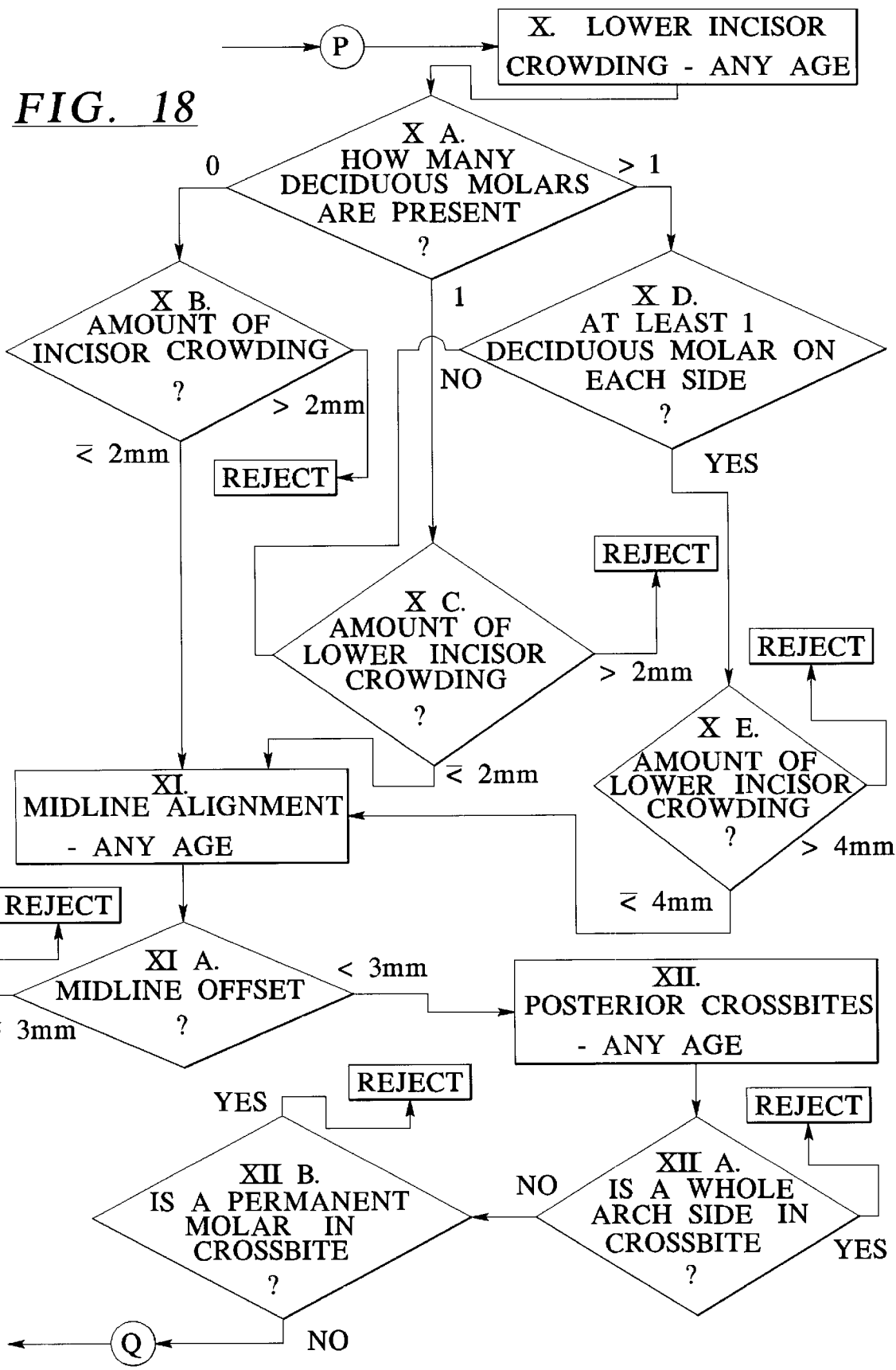
Figure 19:
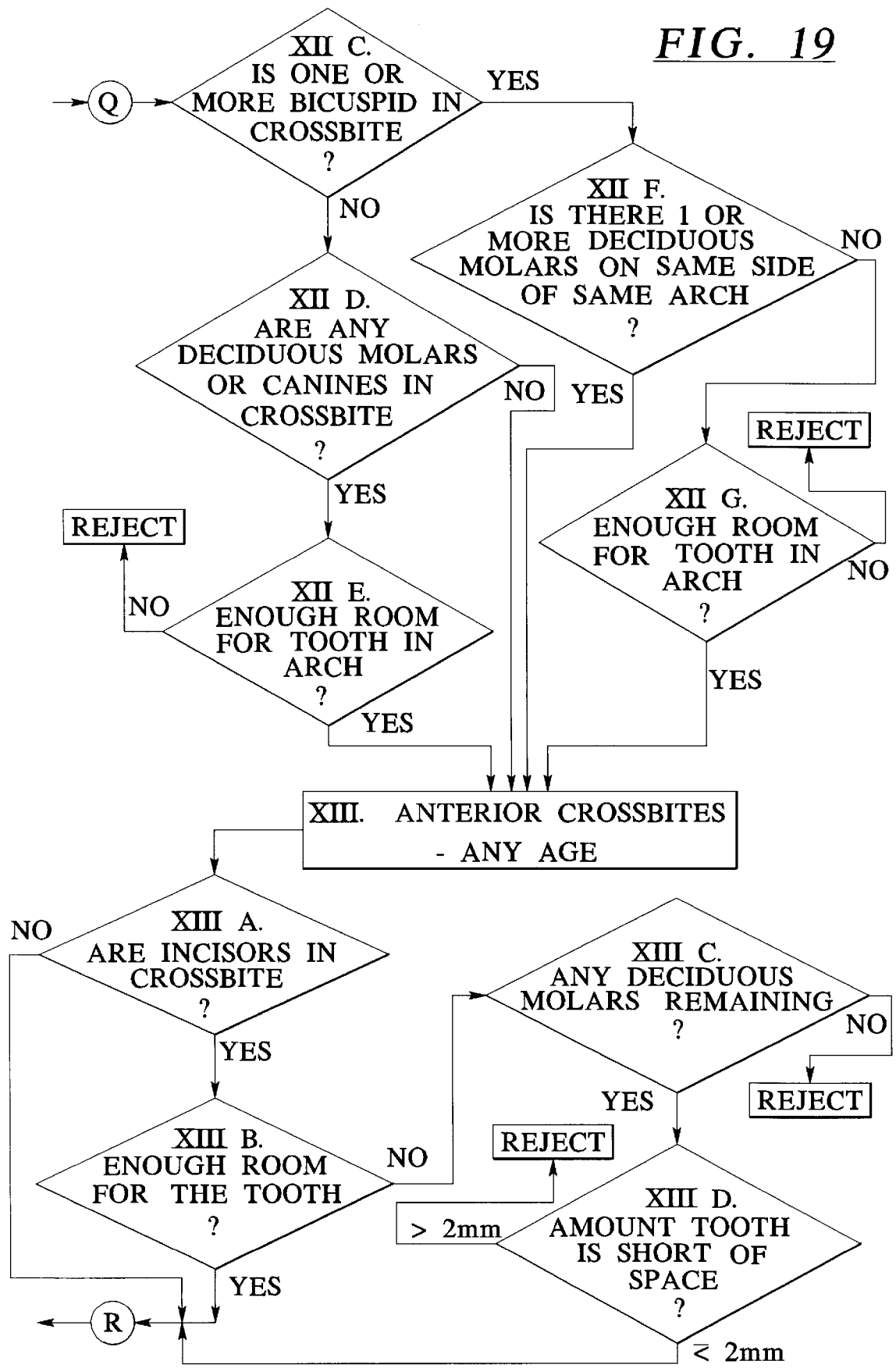
Figure 20:
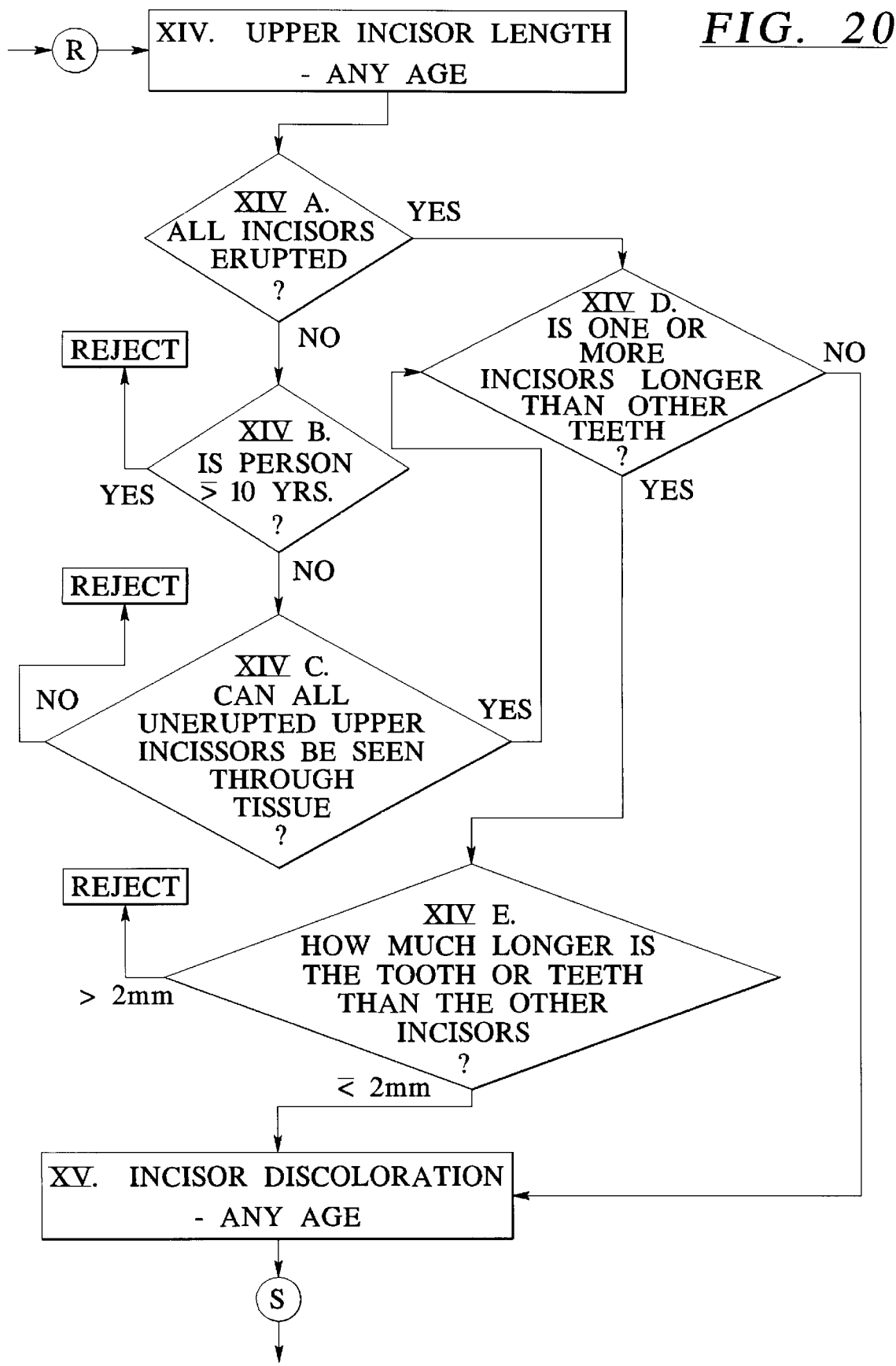
Figure 21:
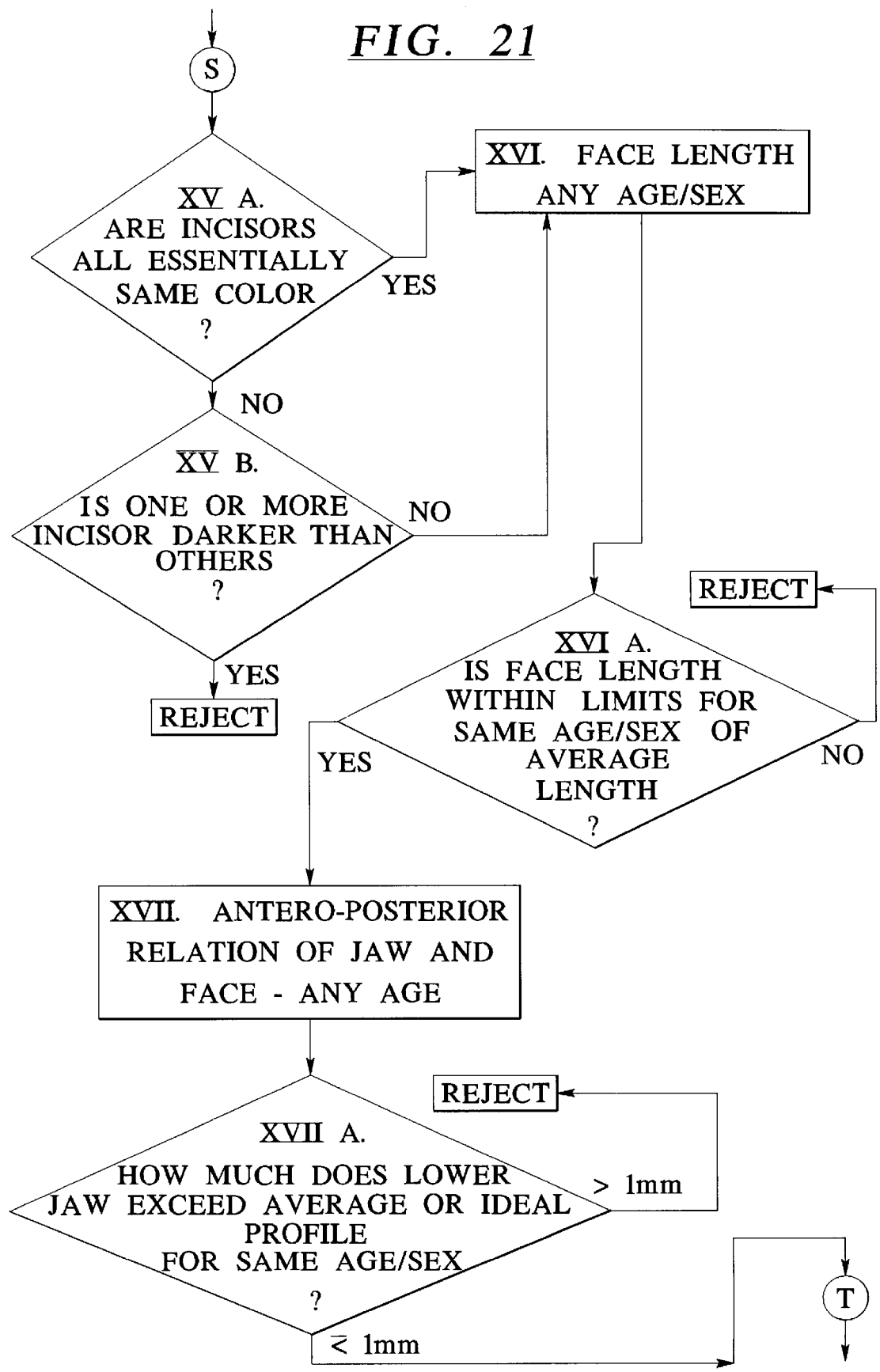
Figure 22:
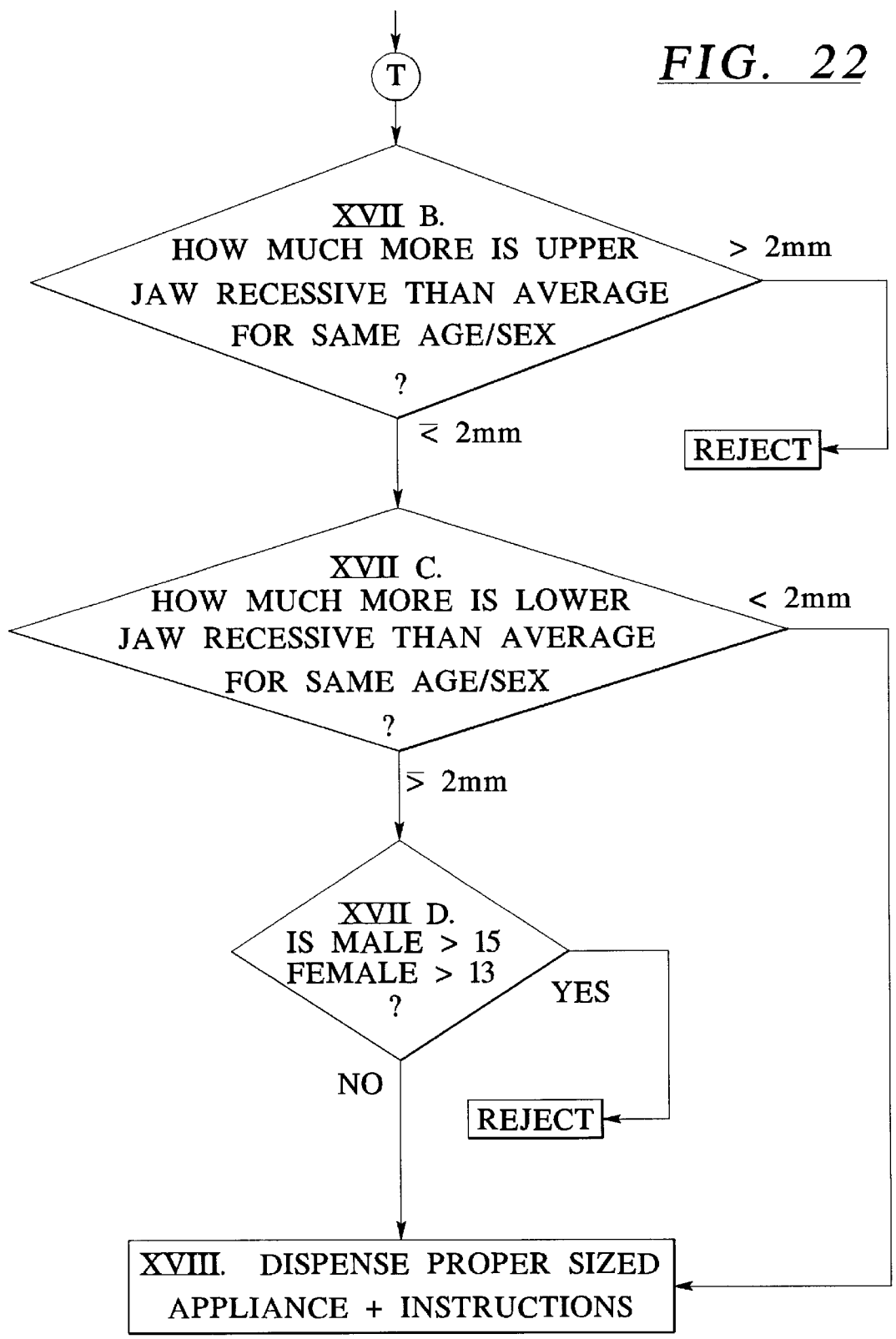

Referring now to FIG. 12, the diagnostic Program Y begins at Step I in determining the presence or absence of the patient's teeth based upon the front and lateral intra-oral and upper and lower occlusal views from the cameras. At Step I A the program determines the age and sex of the individual. If the person is a male of 16 years of age or younger or a female of 14 years of age or younger the program proceeds to Step I B. If the individual is a male over 16 or a female over 14 the program continues to Step I F. In Step I F. it is determined whether any permanent incisors are missing. If yes, the patient is rejected. If no, the program proceeds to Step I G. In Step I B, the program diagnosis whether the patient's upper central incisors and all four lower incisors are permanent teeth and erupted. If no, the program proceeds to Step I H described below and if yes, the program proceeds to Step I C. In this step, the program diagnosis whether any posterior teeth of the individual are missing. If there are no posterior teeth missing, the program proceeds to Step II. If there are one or more posterior teeth missing and the one or more missing teeth are permanent teeth the program continues to Step I E described below. If the posterior teeth missing in the individual are deciduous teeth, the program proceeds to Step D.

In Step D the program diagnosis whether the missing permanent teeth will erupt without crowding in the particular arch of the patient. If the answer is no and crowding will be caused by the erupting permanent missing teeth the patient is rejected for further treatment. If the missing permanent teeth will erupt without crowding the program continues to Step II. In Step I E for an individual having one or more posterior teeth missing which are permanent teeth, the program determines whether the male is 13 years of age or younger or the female is 12 years of age or younger. If so, the program will continue to Step II. If not, the program will continue to Step I I described below.

For males over 14 and females over 16 in Step I G, the program determines whether any posterior teeth of the individual are missing. If no, the Program will continue to Step II. If the individual has posterior teeth missing, the program continues to Step I I. In this step the program determines how much space has closed in the arch having the missing tooth or teeth. If the space has closed more than 2 mm; the patient is rejected for further treatment and if the space has closed less than or equal to 2 mm the program continues to Step II.

In Step I H the program determines whether any permanent incisors are missing from the individual's mouth. This diagnosis is made on an individual where it was determined in Step I B that the upper central and all four lower incisors were not yet permanent teeth. If any permanent incisors are missing from the individual the patient is rejected for further treatment. If no permanent incisors are missing, the program continues to Step I J. In this step, the Program Y diagnoses whether there is enough space for the upper lateral teeth to erupt in their respective arches without crowding of other teeth. If not, the patient is rejected for further treatment and if so the program continues to Step II.

The Program Y diagnoses in Step II the presence or absence of an open-bite in a patient of any age and sex using the front and lateral intra-oral views. In Step II A, the program diagnoses whether an open-bite in the incisors is present and if so the patient is rejected for further treatment. If no open-bite exists, the incisors are in an end-to-end condition or into an overbite condition and the program proceeds to Step III.

The Program Y next diagnoses in Step III, the presence or absence of an overbite from the same front and lateral intra-oral views. In Step III A the program determines again whether the female is 14 years of age or younger or the male patient is 16 years of age or younger. If yes, the program continues to Step III D and if the female patient is over 14 or the male patient is over 16 the program continues to Step III B. In Step III B the program diagnosis the amount of overbite in the individual. If the amount of overbite in the female over 14 or the male over 16 is greater than 5 mm the patient is rejected for further treatment. If the amount of overbite is 2 mm or greater and 5 mm or less the program continues to Step IV. If the amount of overbite is less than 2 mm the program continues to Step III C. In this step the program diagnosis the amount of incisal spacing of the individual. If the individual has more than 2 mm of space in the incisal area the patient is rejected for further treatment. If the individual has less than or equal to 2 mm of incisal spacing the program continues to Step IV.

In Step III D for females of 14 or under and males of 16 or under the program diagnosis the amount of overbite. If the amount of overbite is less than or equal to 5 mm the program continues to Step IV and if the amount of overbite in the individual is greater than 5 mm the program continues to Step III E. In Step III E the program determines whether the female is less than 11 years of age and the male is less than 15 years of age. If not the patient is rejected for further treatment and if so the program continues to Step III F. In this step the program diagnosis whether the amount of overbite is less than 7 mm in the patient and if so the program continues on to Step IV. If the patient has an overbite of 7 mm or greater the program continues to Step III G wherein the program determines whether the female is under 9 years of age and the male is under 12 years of age. If not, the patient is rejected for further treatment and if so the program next determines in Step III H whether the amount of overbite in the individual is less than 9 mm. If the amount of overbite is less than 9 mm the program continues to Step IV and if not the program continues to Step III I. In this step the program next determines whether the female is less than 8 years of age or the male is less than 11 years of age and if not the patient is rejected for further treatment and if so the program continues to Step IV.

The diagnostic Program Y will then determine in Step IV the presence or absence of an overjet condition from the front and lateral intra-oral views. In Step IV A the program again determines whether the patient is female 14 years of age or younger or male 16 years of age or younger and if so continues to Step IV E. If the patient is a female over 14 or a male over 16 the program continues to Step IV B wherein it diagnoses the amount of overjet in the individual. If the amount of overjet is greater than 5 mm the patient is rejected for further treatment. If the amount of overjet in the individual is less than 2 mm the program continues to Step IV C wherein the program determines the amount of incisal spacing in the individual. If the amount of spacing is greater than 2 mm the patient is rejected for further treatment and if the amount of spacing is less than or equal to 2 mm the program continues to Step V. If the amount of overjet in the individual is 2 mm or greater and 5 mm or less the program the continues to Step IV D.

In Step IV D the amount of incisal spacing is again determined for the individual wherein if the spacing is greater than 4 mm the patient is rejected for further treatment and if the spacing is less than or equal to 4 mm the program continues to Step V.

For individual's age and sex requirements in Step IV A where the female is over 14 and male is over 16, the program then proceeds to Step IV E wherein the program again determines the amount of overjet of the patient. If the amount of overjet in the individual is less than 2 mm the program continues to Step IV F for determining the amount of incisal spacing. In this step if the amount of incisal spacing is greater than 2 mm the patient is rejected for further treatment and if less than or equal to 2 mm the program continues to Step V.

If the amount of overjet in these individuals in Step IV E (females over 14, males over 16) is 2 mm or greater and 5 mm or less the program continues to Step IV G wherein the amount of incisal spacing is again determined. If the spacing of the individual is greater than 4 mm they are rejected for further treatment and if less than or equal to 4 mm the program again continues to Step V.

If the amount of overjet in these individuals of Step IV E is greater than 5 mm the program continues to Step IV H wherein the program further determines whether a female patient is less than 11 years of age and the male patient is less than 14 years of age. If not, the patient is rejected for further treatment and if so the program continues to Step IV I. In this step the program diagnosis whether the amount of overjet is less than 8 mm and if so the program then continues to Step V and if not the program continues to Step IV J. In this step the program determines whether the female is less than 10 years of age and the male is less than 13 years of age. If not the patient is rejected for further treatment and if so the program continues to Step IV K. In this step the program diagnoses whether the amount of overjet is less than 11 mm and if so the program continues to Step V and if not continues to Step IV L. In this step the program determines whether the female patient is less than 9 years of age and a male patient is less than 10 years of age and if not the patient is again rejected and if so the program continues to Step V.

In Step V the diagnostic Program Y determines the amount of upper incisal spacing using the front or lateral intra-oral views and upper occlusal view from the camera. In Step V A the program determines whether the patient is female and 14 years of age or younger or male and 16 years of age or younger. If so the program continues to Step V D described below and if not this program continues to Step V B. In Step V B the program determines the amount of upper incisal spacing of the individual. If the amount of spacing is less or equal to 3 mm the program continues to Step VI and if the amount of spacing is greater than 3 mm the program continues V C. In this step the program diagnosis whether there is crowding in the other upper teeth which would permit the spacing of the teeth to even out if the incisal spacing were corrected. Therefore if there is crowding in the upper teeth the program continues to Step VI and if there is no crowding in the upper teeth the patient is rejected for further treatmentif the overjet in Step V F is less than 3. If more, the program proceeds to Step VI. If a female patient is over 14 years of age or a male patient is over 16 years of age the program in Step V D determines the amount of upper incisal spacing. If the individual has less than or equal to 3 mm of space in the upper incisors the program continues to Step VI. If the patient has more than 5 mm of spacing in the upper incisors the patient is rejected for further treatment. If the amount of upper incisal spacing is greater than 3 mm but less than or equal to 5 mm the program continues to Step V E. In this step the program again determines whether there is crowding in the upper teeth and if so continues to Step VI. If there is no additional crowding in the upper teeth and the overjet is 3–5 mm in Step V G, program goes to Step VI, if no the patient is rejected for further treatment.

The diagnostic Program Y next determines in Step VI the amount of lower incisal spacing utilizing the front or lateral intra-oral and lower occlusal views. This determination is made regardless of the age and sex of the patient in Step VI A. If the amount of spacing is 3 mm or less, the program continues to Step VII. If the amount of the incisal spacing is greater than 3 mm, the program continues to Step VI B and determines whether there is some posterior crowding of teeth in the patient. If so the program continues to Step VII and if not, the patient is rejected for further treatment. If the amount of spacing is greater than 5 mm, the patient is also rejected for further treatment.

In Step VII the diagnostic Program Y determines the amount of posterior spacing of the patient's teeth using the lateral intra-oral and lower occlusal views. In Step VII A the program determines whether the patient is a female of 12 years of age or younger or a male of 14 years of age or younger and if so proceeds to Step VII D. If the individual is a female older than 12 or a male older than 14 the program continues to Step VII B. In this step the program determines the amount of posterior tooth spacing on either side of a particular arch. If the amount of spacing in the posterior teeth is greater than 5 mm the patient is rejected for further treatment. If the amount of spacing is less than or equal to 2 mm the program continues to Step VIII. If the amount of posterior tooth spacing in a given arch is greater than 2 mm but less than or equal to 5 mm the program continues to Step C in which the diagnosis is made as to the amount of incisal crowding in that particular arch. If the amount of crowding is 4 mm or less the program then continues to Step VIII and if the amount of crowding is greater than 4 mm the patient is rejected for further treatment.

In Step VII D for female patients 12 or under or male patients 14 or under the diagnostic program determines whether there are any deciduous molars still present in the individual's mouth. If there are the program continues to VII F and if there are no deciduous molars present the program continues to Step VII E. In this step the program determines the amount of posterior tooth spacing on either side of an arch and if the amount of space is greater than 2 mm the patient is rejected and if the amount of posterior tooth space is 2 mm or less the program continues to Step VIII.

The program in Step VII F determines the amount of posterior tooth spacing for a given arch and if the amount of spacing is greater than 2 mm the patient is rejected and if 2 mm or less the program continues to Step VII G. In this step the program diagnosis the amount of incisal crowding for the particular arch having the posterior tooth space and if the amount of crowding is greater than 5 mm the patient is rejected. If the amount of crowding in the incisors is 5 mm or less the program then continues to Step VIII.

The diagnostic Program Y next determines in Step VIII the amount of posterior tooth crowding using the lateral intra-oral views and the lower occlusal views. This diagnosis is done regardless of age or sex of the patient. In Step VIII A the program diagnoses whether the individual has any deciduous molars present. If yes the program continues to Step VIII C and if no the program continues to Step VIII B. In Step VIII B the program diagnoses the amount of crowding in the posterior teeth. If a given side of an arch has greater than 1 mm of crowding the patient is rejected for further treatment and if 1 mm or less the program continues to Step IX. If the patient has one or more deciduous molars remaining in Step VIII C the program diagnoses the amount of crowding in each arch having one or more deciduous molars. If more than 4 mm the patient is rejected for treatment and if less than 4 mm the program again continues to Step IX.

The diagnostic program next diagnoses the amount of crowding of the upper incisors in Step IX using the lateral intra-oral and upper occlusal views and does so for patients of any age or sex. In Step IX A the program determines the number of upper deciduous molars present in the individuals mouth. If no deciduous molars are present the program continues to Step IX B and diagnoses the amount of crowding in the upper incisors. If greater than 2 mm the patient is rejected and if 2 mm or less of crowding the program continues to Step X. If the patient has only one deciduous molar present the program continues to Step IX C and diagnoses the amount of crowding in the upper incisors. Again if the patient has greater than 2 mm of crowding they are rejected and if 2 mm or less the program continues to Step X. If the patient has more than 1 deciduous molar present the program continues to Step IX D and diagnoses whether there is at least one deciduous molar on each side of the upper arch. If no the program returns to Step IX C and rejects the patient if greater than 2 mm of incisor crowding in the upper arch and then continues to Step X if 2 mm or less of upper incisor crowding. If the patient has at least one deciduous molar in each side of the upper arch the program continues to Step IX E and diagnoses the amount of crowding in the upper incisors. If greater than 4 mm the patient is rejected and if 4 mm or less the program continues to Step X.

The diagnostic Program Y next diagnoses in Step X the lower incisor crowding condition using the lateral intra-oral views and lower occlusal view. This determination is also made regardless of the age and sex of thee patient. In Step X A the program determines the number of deciduous molars present in the lower arch. If the individual has no deciduous molars present the program continues to Step X B and determines the amount of crowding in the lower incisors. If the individual has more than 2 mm of crowding they are rejected for further treatment and if they have 2 mm or less of crowding the program continues to Step XI.

If the individual has only one deciduous molar present in the lower arch the program continues to Step X C and diagnoses the amount of crowding in the lower incisors. Again if more than 2 mm of crowding the patient is rejected and if 2 mm or less the program continues to Step XI. If the individual has more than 1 deciduous molar present in the lower arch the program continues to Step X D. In this step the program diagnoses whether at least one deciduous molar is present on each side of the lower arch and if yes continues to Step X E. If not the program returns to Step X C and rejects the patient with more than 2 mm of incisor crowding in the lower arch and continues on to Step XI if 2 mm or less of crowding in the lower incisors. In Step X E if the individual has more than 4 mm of crowding of the lower incisors they are rejected for further treatment and if 4 mm or less the program again continues to Step XI.

In Step XI the program diagnoses the midline alignment using the front intra-oral view of the patient and does so for individuals of any age or sex. In Step XI A, the program diagnoses whether the patient's midline is offset by less than 3 mm the program continues to Step XII. If the patient's midline is off by 3 mm or more, the patient is rejected for further treatment.

The program next diagnoses in Step XII the posterior cross-bite condition for patients of any age or sex using the lateral intra-oral and front intra-oral views and occlusal views.

In Step XII A the program diagnoses whether a whole arch side is in cross-bite and if so the patient is rejected and if not the program continues to Step XII B. In this step the program diagnoses whether one or more permanent molars are in cross-bite and if so the patient is rejected for further treatment and if not the program continues to Step XII C. In this step the program diagnoses whether one or more bicuspids is in cross-bite and if so the program continues to Step XII F and if not continues to Step XII D.

In Step XII D the program diagnoses whether there are any deciduous molars or canine teeth in cross-bite and if not the program continues to Step XIII. If the individual has one or more deciduous molars or canines in cross-bite the program continues to Step XII E which diagnoses whether there is enough room for the permanent molar or canine which will replace the deciduous tooth in cross-bite. If there is not enough room the program rejects the patient for further treatment and if there is enough room the program continues to Step XIII.

In Step XII F, if the patient had one or more bicuspids in cross-bite the program then determines whether the individual has one or more deciduous molars on the same side of the same arch which has the bicuspid or bicuspids in cross-bite. If so the program continues to Step XIII and if not continues to Step XII G. In this step the program determines whether there is enough room for the permanent teeth which will replace the one or more deciduous molars and if so the program continues to Step XIII and if not the program rejects the patient.

The diagnostic Program Y in Step XIII diagnoses whether the individual has an anterior tooth cross-bite condition for those of any age or sex using the front and lateral intra-oral views and occlusal view. In Step XIII A the program diagnoses whether any incisors are in cross-bite and if not the program continues to Step XIV. If the incisors of the individual are in cross-bite the program continues to Step XIII B for diagnosing whether there is enough room for the tooth or teeth in the arch which is in cross-bite. If so the program continues to Step XIV and if not continues to Step XIII C. In this step the program diagnoses whether any deciduous molars remain in the individual's mouth. If not the patient is rejected for further treatment and if so the program continues to Step XIII D. In this step the program determines whether the tooth or teeth in cross-bite is short of space. If the tooth is short of space by more than 2 mm the patient is rejected for further treatment. If the tooth is short of space by 2 mm or less the program continues to Step XIV.

In Step XIV the diagnostic Program Y diagnoses the length of the upper incisors using the front intra-oral view and does so regardless of the patient's age or sex. The diagnoses includes comparison of incisor length relative to one another and relative to the other teeth of the individual. In Step XIV A the program diagnoses whether all incisors have erupted in the individual's mouth and if they have the program continues to Step XIV D and if they have not continues to Step XIV B. In Step XIV B the program diagnoses whether the individual is 10 years old or older and if so rejects the individual for further treatment. If not the program continues to Step XIV C and diagnoses whether all unerupted upper incisors are seen coming through tissue and if not, the patient is rejected for further treatment. If so, the program then continues to Step XIV D.

In Step XIV D the program diagnoses whether one or more incisor is longer than other teeth in the individual's mouth and if not continues to Step XV. If one or more is longer than the other incisor teeth in the mouth the program then continues to Step XIV E and diagnoses how much longer the tooth or teeth is relative to its respective other incisors. If more than 2 mm the patient is rejected for further treatment and if 2 mm or less the program continues to Step XV.

The diagnostic program next diagnoses in Step XV whether there is any discoloration of the incisors for patients of any sex or age and using the front and lateral intra-oral views. In Step XV A, the program diagnoses whether the incisors are essentially all of the same color, and if so continues to Step XVI. If not, the program continues to Sep XV B and determines if one or more incisor is found to be darker than the other incisors, the patient is rejected for treatment. If so, the patient is rejected and if not, the program continues to Step XVI.

In Step XVI the diagnostic Program Y measures the length of the face of the patient using the front face and lateral profile views and does so for patients of any age or sex. In Step XVI A, if the patient's face length as measured from the top of the nose to the bottom of the chin exceeds programmed limits for median or average patients of the same age and sex as the patient, the individual is rejected for further treatment. If the individual's face length falls within the program limits (plus or minus two standard deviations) for a child of like age and sex the program continues to Step XVII.

In Step XVII the diagnostic Program Y diagnoses the antero-posterior relation of the jaw and face of the individual regardless of age or sex. The program compares the characteristics of the individual to the average characteristics for one or like age and sex. The program diagnoses the individual's characteristics using the lateral profile facial view. In Step XVII A the program determines how much the lower jaw of the individual exceeds the average profile for one of the same age and sex. If the individual's lower jaw exceeds the ideal profile by more than 1 mm they are rejected for treatment and if the lower jaw exceeds the profile by 1 mm or less the program continues to Step XVII B. In this step the program diagnoses how much the upper jaw is recessive compared to an average person of like age and sex. If the upper jaw of the individual is recessive more than 2 mm they are rejected for treatment and if 2 mm or less the program continues to Step XVII C. In this step the program diagnoses how much the individual's lower jaw is recessive as compared to an average person of like age and sex. If less than 2 mm the program then continues to Step XVIII and if 2 mm or more the program continues to XVII D. In this step the program determines whether the male is over 15 years or age or the female is over 13 years of age and if so they are rejected for treatment. If not the program continues to Step XVIII.

In Step XVIII the diagnostic Program Y will review all the data collected during each step of the program and if the patient has not yet been rejected and is found to be a candidate for orthodontic correction, the machine selects and dispenses a proper fitting appliance. The program compares digital images of the patient's actual mouth taken from the various camera views and using preprogrammed size and correction data for the various appliances selects the proper appliance. The machine then dispenses the appliance with instructions for wear. The instructions include wear information for both the correction stage and also for the retention phase.

For the above described Programs X and Y the computer for each step in the diagnostic procedure compares the digital data taken from the digital images of the individual and to one of two data sets or a combination of the two data sets. The first data set includes the upper and lower limits and averages of the specific characteristics such as overbite, overjet, crowding or tooth rotation to be programmed into the electronics. The patient's video images are compared to these programmed limits for age and sex of the patient. If any of the patient's characteristics fall outside of the limit parameters for a particular condition such as, for example overbite, the patient would be rejected by the program as described above. Another data set may be downloaded into the computer program including actual digital images of individuals of various ages for both sexes to digitally compare to the video images of the patient. The program compares the digital data of the patient to the programmed digital image of the ideal patient and either accepts or rejects the patient for treatment depending on the amount of variation between the two images. In either method of comparison, the record of the patient will be stored in the computer memory for legal purposes and as medical records for potential further treatment or for upload by medical personnel.

When the apparatus selects an appliance and dispenses it to the patient, the instructions may be provided in various ways. One way is to provide written instructions on paper dispensed from the machine. The instructions are provided in the appropriate language of the country in which the machine is installed. The machine may be programmed to communicate in more than one language if necessary. The instructions are intended to provide the patient with the information on how to wear the appliance, the duration of wear each day, the duration of overall treatment, the necessity and duration of specific exercises which the patient may need to perform for treatment, the wear instructions for proper retention after correction is achieved, and other instructions as needed.

If the patient has been rejected for some reason, the machine may print out this information along with instructions for getting additional treatment from a dental practitioner or merely for indicating the reasons why the patient cannot be treated now or will not be treated in the future. The apparatus may even be programmed for retaining a list of practitioners in a particular area and may recommend in the instructions to the patient a particular practitioner to perform the service recommended. For example, if the patient needs to a have a tooth pulled in order to continue treatment, the machine may indicate who in the area may perform this service and where they are located.

While a preferred embodiment has been shown and described, modifications, changes or additions to diagnostic principles and other changes in the efficiency and completeness to the diagnostics and the program may be apparent to those skilled in the art which shall fall within the spirit and scope of the invention. It is also possible that single size or one-size fits all appliances are dispensed in the same manner as described. It is intended that such modifications and changes be covered by the appended claims.

I claim as my invention:

1. An apparatus for diagnosing orthodontic conditions in a mouth of an individual, the apparatus comprising:

an outer case;

a user interface disposed on the outer case adapted to provide information to diagnostic hardware positioned within the outer case including at least one digital camera adapted to take images of the individual's teeth and mouth from a plurality of angles;

electronic circuitry preprogrammed with statistical data representing sample orthodontic conditions for comparison to actual data collected by the diagnostic hardware representing the orthodontic conditions of the individual and transmitted to said electronic circuitry and further adapted to diagnose whether the orthodontic conditions of the individual are correctable; and means for dispensing instructions via the user interface to the individual to inform of the results of the diagnosis and to instruct how to correct the orthodontic conditions.

2. The apparatus according to claim 1, wherein the at least one digital camera is mounted to the outer case and is movable to preprogrammed positions relative to the outer case to take the plurality of images.

3. The apparatus according to claim 1, wherein the at least one digital camera is stationary relative to the outer case and the individual moves to acquire the plurality of angles.

4. The apparatus according to claim 1, wherein the user interface comprises a display screen for providing information to the individual.

5. The apparatus according to claim 1, wherein the user interface comprises a keypad disposed on the outer case for receiving information from the individual.

6. The apparatus according to claim 5, wherein the user interface further comprises a display screen disposed on the outer case to display information for the individual.

7. The apparatus according to claim 4, wherein the display screen is a touch screen adapted for providing information to the individual and for receiving information from the individual.

8. The apparatus according to claim 1, wherein the statistical data represents a plurality of orthodontic conditions from a cross-section of individual of various age, sex and orthodontic conditions.

9. The apparatus according to claim 1, wherein the statistical data represents upper and lower limits for each of a plurality of orthodontic conditions diagnosed by the apparatus.

10. The apparatus according to claim 1, wherein the statistical data comprises actual digital models representing a plurality of orthodontic conditions from a cross-section of individuals of various age, sex and orthodontic conditions.

11. The apparatus according to claim 1, further comprising an appliance storage chamber disposed within the outer case storing therein a plurality of prefabricated orthodontic corrective appliances of various size.

12. The apparatus according to claim 11 further comprising an appliance dispenser adapted to select one of the prefabricated orthodontic corrective appliances based upon the diagnosed orthodontic condition of the individual and to dispense the selected prefabricated appliance to the individual.

13. The apparatus according to claim 1, further comprising an appliance storage chamber disposed within the outer case storing therein a plurality of one-size fits all appliances, and dispenser adapted to dispense the appliances.

14. The apparatus according to claim 1, further comprising a payment device carried on the outer case for receiving payment information from the individual.

15. The apparatus according to claim 14, wherein the payment device comprises a magnetic stripe reader for reading a payment card carrying thereon a magnetic stripe.

16. The apparatus according to claim 15, wherein the electronic circuitry is further preprogrammed to receive the payment information from the magnetic stripe reader and further adapted to communicate with the user interface for providing payment information to the individual.

17. The apparatus according to claim 15, wherein the payment device is adapted to credit payment from a credit card having thereon a magnetic stripe.

18. The apparatus according to claim 15, wherein the payment device is adapted to credit payment from a debit card having thereon a magnetic stripe.

19. The apparatus according to claim 1, wherein the electronic circuitry is preprogrammed to diagnose at least orthodontic conditions of the individual such as presence or absence of permanent teeth, presence or absence of deciduous teeth, overbite, overjet, cross-bite, open-bite, gummy smile, tooth crowding, tooth rotation and tooth spacing.

20. The apparatus according to claim 19, wherein the electronic circuitry is preprogrammed to compare the statistical information for each of the orthodontic conditions relative to the actual orthodontic condition of each of the orthodontic conditions of the individual.

21. The apparatus according to claim 1, further comprising an adjustable seat carried on the outer case permitting the individual to sit so that the mouth and teeth of the individual is properly positioned relative to the diagnostic hardware.

22. The apparatus according to claim 1, further comprising a support carried on the outer case for properly positioning the mouth and teeth of the individual relative to the diagnostic hardware.

23. The apparatus according to claim 22, wherein the support comprises a chin rest and a forehead rest.

24. A method for diagnosing orthodontic conditions of an individual, the method comprising the steps of:

providing a diagnostic apparatus having diagnostic hardware including at least one digital camera adapted to take a plurality of images of the individual's teeth and mouth;

providing a user interface on the apparatus to display information for the individual and to receive information from the individual;

providing electronic circuitry within the apparatus;

preprogramming the electronic circuitry with statistical data representing sample orthodontic conditions;

positioning the individual relative to the diagnostic hardware;

taking a plurality of images of the individual's teeth and mouth from the diagnostic hardware representing actual data of the orthodontic conditions of the individual;

comparing the actual data to the preprogrammed statistical data with the electronic circuitry;

determining via the apparatus whether the orthodontic conditions of the individual are correctable; and dispensing instructions from the apparatus to the individual to instruct how to correct the orthodontic conditions diagnosed by the apparatus.

25. The method according to claim 24, further comprising the steps of storing a plurality of prefabricated orthodontic appliances within the apparatus, selecting one of the plurality of prefabricated orthodontic appliances, and dispensing the selected prefabricated orthodontic appliance to the individual along with instructions for proper wear to correct the orthodontic conditions diagnosed by the apparatus.

26. The apparatus according to claim 24, wherein the step of diagnosing further comprises determining how old the individual is through the user interface of the apparatus and then proceeding to a first or a second diagnostic program of the electronic circuitry depending upon the age of the individual.

27. The method according to claim 26, wherein the step of diagnosing further comprises diagnosing the orthodontic conditions of the individual including at least presence or absence of deciduous teeth, presence or absence of permanent teeth, overbite, overjet, open-bite, cross-bite, tooth spacing, tooth crowding, and tooth rotations and comparing each orthodontic condition of the individual to a corresponding portion of the preprogrammed statistical data for each respective orthodontic condition and determining whether each of the orthodontic conditions of the individual are correctable.

* * * * *